US010745752B2

(12) United States Patent
West et al.

(10) Patent No.: US 10,745,752 B2
(45) Date of Patent: Aug. 18, 2020

(54) METHODS FOR TELOMERE LENGTH AND GENOMIC DNA QUALITY CONTROL ANALYSIS IN PLURIPOTENT STEM CELLS

(71) Applicant: LINEAGE CELL THERAPEUTICS, INC., Carlsbad, CA (US)

(72) Inventors: Michael D. West, Mill Valley, CA (US); Karen B. Chapman, Mill Valley, CA (US); Walter D. Funk, Hayward, CA (US)

( * ) Notice: Subject to any disclaimer, the term of this patent is extended or adjusted under 35 U.S.C. 154(b) by 144 days.

(21) Appl. No.: 15/162,543

(22) Filed: May 23, 2016

(65) Prior Publication Data

US 2017/0335392 A1    Nov. 23, 2017

Related U.S. Application Data

(63) Continuation of application No. 14/876,779, filed on Oct. 6, 2015, now abandoned, which is a continuation of application No. 13/579,875, filed as application No. PCT/US2011/025316 on Feb. 17, 2011, now abandoned.

(60) Provisional application No. 61/312,580, filed on Mar. 10, 2010, provisional application No. 61/305,506, filed on Feb. 17, 2010.

(51) Int. Cl.
    *C12Q 1/6881*    (2018.01)
(52) U.S. Cl.
    CPC ..... *C12Q 1/6881* (2013.01); *C12Q 2600/158* (2013.01)
(58) Field of Classification Search
    CPC .... C12Q 1/668; C12Q 2600/158; C12N 5/00; C12N 5/06; C12N 5/0603; C12N 5/0606
    See application file for complete search history.

(56) References Cited

U.S. PATENT DOCUMENTS

2010/0167404 A1    7/2010  West et al.
2013/0011918 A1    1/2013  West et al.

FOREIGN PATENT DOCUMENTS

WO    2007/062198 A1    5/2007

OTHER PUBLICATIONS

Suhr et al. PloS One, 4(12): pp. 1-9, Dec. 2009.*
Forsyth et al., Rejuvenation Research, 11(1): 5-17, 2007.*
Assou et al., BMC Genomics, 10(10): 1-15, Jan. 8, 2009.*
Amabile et al., Induced pluripotent stem cells: current progress and potential for regenerative medicine. Trends Mol Med. Feb. 2009;15(2):59-68.
Amit et al., Clonally derived human embryonic stem cell lines maintain pluripotency and proliferative potential for prolonged periods of culture. Dev Biol. Nov. 15, 2000;227(2):271-8.
Binet et al., WNT16B is a new marker of cellular senescence that regulates p53 activity and the phosphoinositide 3-kinase/AKT pathway. Cancer Res. Dec. 15, 2009;69(24):9183-91.
Bodnar et al., Extension of life-span by introduction of telomerase into normal human cells. Science. Jan. 16, 1998;279(5349):349-52.
Cawthon et al., Association between telomere length in blood and mortality in people aged 60 years or older. Lancet. Feb. 1, 2003;361(9355):393-5.
Chin et al., Induced pluripotent stem cells and embryonic stem cells are distinguished by gene expression signatures. Cell Stem Cell. Jul. 2, 2009;5(1):111-23.
Chiu et al., Differential expression of telomerase activity in hematopoietic progenitors from adult human bone marrow. Stem Cells. Mar. 1996;14(2):239-48.
Cibelli et al., Somatic Cell Nuclear Transfer in Humans: Pronuclear and Early Embryonic Development. e-biomed: The Journal of Regenerative Medicine. Nov. 26, 2001;2;25-31.
Feng et al., Hemangioblastic derivatives from human induced pluripotent stem cells exhibit limited expansion and early senescence. Stem Cells. Apr. 2010;28(4):704-12.
Feng et al., The RNA component of human telomerase. Science. Sep. 1, 1995;269(5228):1236-41.
Freberg et al., Epigenetic reprogramming of OCT4 and NANOG regulatory regions by embryonal carcinoma cell extract. Mol Biol Cell. May 2007;18(5):1543-53.
Hayflick et al., The serial cultivation of human diploid cell strains. Exp Cell Res. Dec. 1961;25:585-621.
Huang et al., Improving cell therapy—experiments using transplanted telomerase-immortalized cells in immunodeficient mice. Mech Ageing Dev. Jan. 2007;128(1):25-30.
Klimanskaya et al., Derivation and comparative assessment of retinal pigment epithelium from human embryonic stem cells using transcriptomics. Cloning Stem Cells. 2004;6(3):217-45.
Lanza et al., Prospects for the use of nuclear transfer in human transplantation. Nat Biotechnol. Dec. 1999;17(12)1171-4.
Lanza et al., Regeneration of the infarcted heart with stem cells derived by nuclear transplantation. Circ Res. Apr. 2, 2004;94(6):820-7.
Lillard-Wetherell et al., Association and regulation of the BLM helicase by the telomere proteins TRF1 and TRF2. Hum Mol Genet. Sep. 1, 2004;13(17):1919-32.
Lund et al., Human embryonic stem cell-derived cells rescue visual function in dystrophic RCS rats. Cloning Stem Cells. 2006 Fall;8(3):189-99.
Mantell et al., Telomerase activity in germline and embryonic cells of Xenopus. EMBO J. Jul. 1, 1994;13(13):3211-7.

(Continued)

*Primary Examiner* — Thaian N. Ton

(57) ABSTRACT

The generation of clinical-grade cell-based therapies from human embryonic stein cells or cells reprogrammed to pluripotency from somatic cells, requires stringent quality controls to insure that the cells have long enough telomeres and resulting cellular lifespan to be clinically useful, and normal gene expression and genomic integrity so as to insure cells with a desired and reproducible phenotype and to reduce the risk of the malignant transformation of cells. Assays useful in identifying human embryonic stem cell lines and pluripotent cells resulting from the transcriptional reprogramming of somatic cells that have embryonic telomere length are described as well as quality control assays for screening genomic integrity in cells expanded and banked for therapeutic use, as well as assays to identify cells capable of abnormal immortalization.

11 Claims, 16 Drawing Sheets

Specification includes a Sequence Listing.

(56) References Cited

OTHER PUBLICATIONS

Marion et al., Telomeres acquire embryonic stem cell characteristics in induced pluripotent stem cells. Cell Stem Cell. Feb. 6, 2009;4(2):141-54.

Mclaren, Mammalian germ cells: birth, sex, and immortality. Cell Struct Funct. Jun. 2001;26(3):119-22.

Nakamura et al., Telomerase catalytic subunit homologs from fission yeast and human. Science. Aug. 15, 1997;277(5328):955-9.

Park et al., Reprogramming of human somatic cells to pluripotency with defined factors. Nature. Jan. 10, 2008;451 (7175):141-6.

Rosler et al., Long-term culture of human embryonic stem cells in feeder-free conditions. Dev Dyn. Feb. 2004;229 (2)259-74.

Roy et al., Functional engraftment of human ES cell-derived dopaminergic neurons enriched by coculture with telomerase-immortalized midbrain astrocytes. Nat Med. Nov. 2006;12(11):1259-68.

Rufer et al., Telomere fluorescence measurements in granulocytes and T lymphocyte subsets point to a high turnover of hematopoietic stem cells and memory T cells in early childhood. J Exp Med. Jul. 19, 1999;190(2):157-67.

Saretzki et al., Downregulation of multiple stress defense mechanisms during differentiation of human embryonic stem cells. Stem Cells. Feb. 2008;26(2):455-64.

Schaetzlein et al., Telomere length is reset during early mammalian embryogenesis. Proc Natl Acad Sci U S A. May 25, 2004;101(21):8034-8.

Schatteman et al., Old bone marrow cells inhibit skin wound vascularization. Stem Cells. Mar. 2006;24(3):717-21.

Shaikh et al., High-resolution mapping and analysis of copy number variations in the human genome: a data resource for clinical and research applications. Genome Res. Sep. 2009;19(9)1682-90.

Shamblott et al., Derivation of pluripotent stem cells from cultured human primordial germ cells. Proc Natl Acad Sci U S A. Nov. 10, 1998;95(23)13726-31.

Shawi et al., Telomerase, senescence and ageing. Mech Ageing Dev. Jan.-Feb. 2008;129(1-2):3-10.

Slagboom et al., Genetic determination of telomere size in humans: a twin study of three age groups. Am J Hum Gene. Nov. 1994;55(5):876-82.

Takahashi et al., Induction of pluripotent stem cells from adult human fibroblasts by defined factors. Cell. Nov. 30, 2007;131(5):861-72.

Taranger et al., Induction of dedifferentiation, genomewide transcriptional programming, and epigenetic reprogramming by extracts of carcinoma and embryonic stem cells. Mol Biol Cell. Dec. 2005;16(12):5719-35.

Thomson et al., Embryonic stem cell lines derived from human blastocysts. Science. Nov. 6, 1998;282(5391)1145-7.

Van Hoof et al., Phosphorylation dynamics during early differentiation of human embryonic stem cells. Cell Stem Cell. Aug. 7, 2009;5(2):214-26.

Vaziri et al., Loss of telomeric DNA during aging of normal and trisomy 21 human lymphocytes. Am J Hum Genet. Apr. 1993;52(4):661-7.

Wang et al., Myc activates telomerase. Genes Dev. Jun. 15, 1998;12(12):1769-74.

Wilmut et al., Viable offspring derived from fetal and adult mammalian cells. Nature. Feb. 27, 1997;385(6619):810-3.

Wright et al., Telomerase activity in human germline and embryonic tissues and cells. Dev Genet. 1996;18(2):173-9.

Yu et al., Induced pluripotent stem cell lines derived from human somatic cells. Science. Dec. 21, 2007;318 (5858):1917-20.

International Search Report and Written Opinion for Application No. PCT/US2011/025316, dated Nov. 21, 2011, 8 pages.

\* cited by examiner

METHODS FOR TELOMERE LENGTH AND GENOMIC DNA QUALITY CONTROL ANALYSIS IN PLURIPOTENT STEM CELLS

REFERENCE TO RELATED APPLICATIONS

This application is a continuation of application Ser. No. 14/876,779, filed Oct. 6, 2015 (abandoned), which is a continuation of Ser. No. 13/579,875, filed Sep. 12, 2012 (abandoned), which is the national stage of International Application No. PCT/US11/25316, filed Feb. 17, 2011, (published as WO 2011/103343) which claims priority to Provisional Application No. 61/312,580, filed Mar. 10, 2010 and Provisional Application No. 61/305,506, filed Feb. 17, 2010, all of which are incorporated herein by reference in their entirety.

INTRODUCTION

In the 19th century August Weismann introduced the parsimonious theory that heredity and the perpetual regeneration of the body in the life cycle stem from an immortal continuum of germ-line cells (Weismann, 1891; McLaren, A 1992, 2001). As a corollary, he postulated a dichotomy of cell fates in metazoans. Germ-line cells were theorized to possess a replicative immortality (though punctuated with alternating meiotic and mitotic events) while somatic cell lineages a finite replicative capacity. The mortal phenotype in somatic cell types, in turn, was implicated in the finite capacity for tissue regeneration and progressive onset of age-related degenerative disease in the human soma over time.

Leonard Hayflick's demonstration that human somatic cells age in vitro (Hayflick & Moorhead, 1961; Hayflick, 1965; Hayflick, 1992) enabled the use cultured somatic cells as an experimental model of senescence and consequently the discovery that telomeric DNA could function as a "replicometer", shortening with age in vivo and in vitro (Olovnikov, 1971; Cooke H J and Smith B A, 1986; Harley, C B et al, 1990). The cloning of the human telomerase components (Feng J. et al, 1995; Nakamura T M et al, 1997) and the demonstration that exogenous expression of the catalytic component of the RNA-dependent DNA polymerase telomerase (TERT) could rescue (immortalize) varied human somatic cell types (Bodnar A G et al, 1998; Vaziri & Benchimol, 1998) has led to the widespread study of telomere biology, including the use of telomere length assays to assess the role of cellular aging in a number of age-related degenerative diseases (West, M. D. 2010).

The validation of the telomere hypothesis of cellular aging has also led to proposals for varied methodologies to reset the clock of cellular aging for therapeutic effect (Shawi & Autexier, 2008). These strategies include the use of telomerized (immortalized) cells in the engineering of tissue grafts (Shay & Wright, 2005; Huang et al, 2007). Because malignant cells often show an immortal phenotype through constitutive telomerase activity (Kim N et al, 1994), means were sought to conditionally express telomerase to extend replicative lifespan where needed and then to repress the activity again to reduce the risk of malignant transformation. The aim to harness this inducible regulation of telomere length and to provide a means of manufacturing all somatic cell types, including embryonic progenitor (EP) cell lineages, stimulated early interest in the isolation of human embryonic stem cells (Thomson J A et al, 1998) and germ cells (Shamblott M J et al, 1998), the former being a well-studied pluripotent and conditionally-immortal stem cell.

The demonstration of the feasibility of somatic cell nuclear transfer (SCNT) in animal cloning (Wilmut & Campbell, 1997) opened the possibility of using SCNT to produce autologous pluripotent and conditionally-immortalized cells ES-like cells (Lanza et al, 1999a,b). The initial report that animals derived by SCNT displayed relatively short telomeres (Shiels et al 1999) led to the initial conclusion that oocyte-mediated reprogramming cytoplasm could reverse differentiation (RD) but not reverse cellular aging (RA). However, subsequent studies using more carefully defined donor cells and improved assays of telomere length demonstrated for the first time that SCNT had the potential to reverse both developmental and cellular aging (RDA) in bovine species (Lanza et al, 2000). Subsequently this observation was extended to other species and other conditions of SCNT (Wakayama et al, 2000; Clark et al, 2003).

While SCNT offers potential as a means a reversing the developmental aging of a human cells to produce young histocompatible cell and tissue grafts, the practicalities of obtaining human egg cells and performing nuclear transfer on a large scale remain daunting. In addition, initial experiments demonstrated that while it was possible to remodel human somatic cell nuclei into pseudo pronuclei, embryonic development generally ceases before blastocyst formation in current protocols, making current studies of human telomere length regulation during reprogramming problematic (Cibelli, J. B. et al, 2001).

More recently, the focus of reprogramming research has shifted to transcriptional reprogramming, that is, the exogenous expression of transcription factors critical to germ-line gene expression such as MYC, KLF4, OCT4, and SOX2 (Takahashi, K. et al, 2007) or LIN28, NANOG, OCT4, and SOX2 (Yu, J. et al, 2007). When introduced into somatic cells, varied combinations of these genes are capable of altering the differentiated state leading to induced pluripotent stem (iPS) cells similar to hES cells. The attraction to facile, cost-effective, and ethically non-problematic means of producing a host of transplantable patient-specific cells useful in the treatment of degenerative diseases such as heart failure, Parkinson's disease, immune senescence and vascular disease has led to numerous studies of iPS cell pluripotency, though there is little research on the effects of transcriptional reprogramming on cellular aging, in particular on telomere length regulation. Initial studies of telomere dynamics in mice (Marion et al, 2009) suggest that while telomere length restoration is delayed compared to the rapid telomere length restoration seen in SCNT, nevertheless, telomeres lengthen over extended propagation in vitro. In the case of human cells, there are contradictory reports as to the proliferative capacity of reprogrammed cells (Suhr et al, 2009; Feng et al, 2010). This may be due in part to the genetic variability in the subtelomeric "X" region of telomere restriction fragments (TRFs) (Levy et al, 1992; Riethman, H et al, 2005) often complicating comparisons of TRF length in differing genotypes. Genetic variation in the subtelomeric region likely contributes to the range of TRF lengths observed in embryonic cells of 12-20 kb and that in cells at the Hayflick limit (typically 5-7 kb). Comparisons with established hES cell lines is additionally complicated by drift in TRF length during propagation in vitro (Rosier E S et al, 2004).

We therefore undertook an analysis of telomere dynamics in transcriptional reprogramming in an isogenic background of the hES-derived clonal embryonic progenitor cell line EN13 such that TRF length can be measured and compared to both the starting somatic cells (EN13) and to the normal hES cells with embryonic TRF length from which EN13 was obtained. The elimination of subtelomeric variability may provide a more sensitive assay of telomere length changes during embryonic transcriptional reprogramming useful in quality control for potential future applications in the treatment of age-related degenerative disease.

SUMMARY

The generation of clinical-grade cell-based therapies from human embryonic stem cells or cells reprogrammed to pluripotency from somatic cells, requires stringent quality controls to insure that the cells have long enough telomeres and resulting cellular lifespan to be clinically useful, and normal gene expression and genomic integrity so as to insure cells with a desired and reproducible phenotype and to reduce the risk of the malignant transformation of cells. Assays useful in identifying human embryonic stem cell lines and pluripotent cells resulting from the transcriptional reprogramming of somatic cells that have embryonic telomere length are described as well as quality control assays for screening genomic integrity in cells expanded and banked for therapeutic use, as well as assays to identify cells capable of abnormal immortalization.

Aspects of the present invention include methods of selecting/identifying cell lines of pluripotent stem cells, e.g., induced pluripotent stem cells (iPS cells) derived by reprogramming somatic cells with transcription factors, capable of restoring near-embryonic telomere restriction fragment length. The pluripotent stem cells may be evaluated for telomere restriction fragment (TRF) length, telomerase activity and/or expression level of one or more genes selected from PCNA, CDC2, MSH2, ZNF146, TERF1 transcript variant 2, VENTX and PRKDC. Pluripotent stem cells having near-embryonic telomere length, telomerase activity and/or levels of expression of the one or more genes equivalent to embryonic/germ cells, e.g., embryonic stem cells, are identified as ones that are clinically useful (i.e., having proliferative capacity suitable for therapeutic purposes). Thus, in certain embodiments, the selected/identified pluripotent cell lines have, or are capable of restoring, telomere restriction fragment length to at least 12, 13, 14, 15, 16, 17, or 18 or more kb. Aspects of the present invention also include compositions of cells produced and selected by the subject methods and systems, kits and computer program products for performing the identification/selection methods.

BRIEF DESCRIPTION OF THE DRAWINGS

FIG. 1A shows Southern blots of DNA isolated from the human ES cell lines MA03, H9, and H1 compared to the human iPS cell lines IMR90-1, BJ1, iPS (FLF), iPS(IMR90)1, iPS(IMR90)-4, iPS(foreskin)-1; and the normal cell types BJ used as the substrate for iPS(foreskin)-1 and BJ1-iPS1; and IMR90 used for IMR90-1, iPS(IMR90)1, iPS(IMR90)-4. FIG. 1B is a bar graph of the calculated mean TRF lengths of the same human ES, iPS, and normal cell DNA samples.

FIG. 2A shows CHAPS extracts of cell pellets normalized by protein content were assayed by the TRAP assay in triplicate. 10% HeLa is a ten-fold dilution of HeLa cells. Lane labeled CHAPS is a solution control. FIG. 2B shows a graph of the quantification of the bands shown in FIG. 2A.

FIG. 6A shows cDNA obtained from the six ReH9 clones which was subjected to RT-PCR and gel electrophoresis analysis using primer sets for the genes shown. FIG. 6B shows ReH9 cell lines, B2 and EH2 which were treated with serum under conditions known to differentiate hES cells and the cells differentiated from H9, B2, and EH2 are designated dH9, dB2, dEH2 respectively. Primer sets for pluripotency markers are shown.

FIG. 8A shows Southern blots hybridized to a telomere-specific probe of the human ES cell line H9, and the H9-derived cell line EN13 at passages 15-17, and the ReH9 clones at extended passage; FIG. 8B shows a graph of calculated mean TRF lengths in H9 and EN13 at passages noted in each blot with best fit linear regression line for the respective passaged ReH9 clones EH1, EH2, EH6, EH6A, and B2. FIG. 8C shows a graph of calculated mean TRF lengths in H9 and EN13 at passages noted on blot with best fit linear regression line for EH3 during serial passage.

FIG. 9A shows telomerase activity which was measured by the TRAP assay protocol. The gels were exposed to phosphorimager screen and the signal was quantified using imagequant software. FIG. 9B shows a graph of two independent experiments performed where the TRAP gels were quantified. The signals were normalized to that of H9 hES cell line (set to 1). EH3, represents a single reading.

FIG. 14A shows expression level of VENTX in numerous cell lines, including ES, iPS, EC and fetal cell lines. FIG. 14B shows VENTX expression levels in numerous mortal differentiated cells and human ES and iPS cell lines. This figure demonstrates that VENTX expression is higher in cells that maintain relatively long telomeres (e.g., hES cells and the iPS cell line EH3).

DEFINITIONS

Figure 1A:
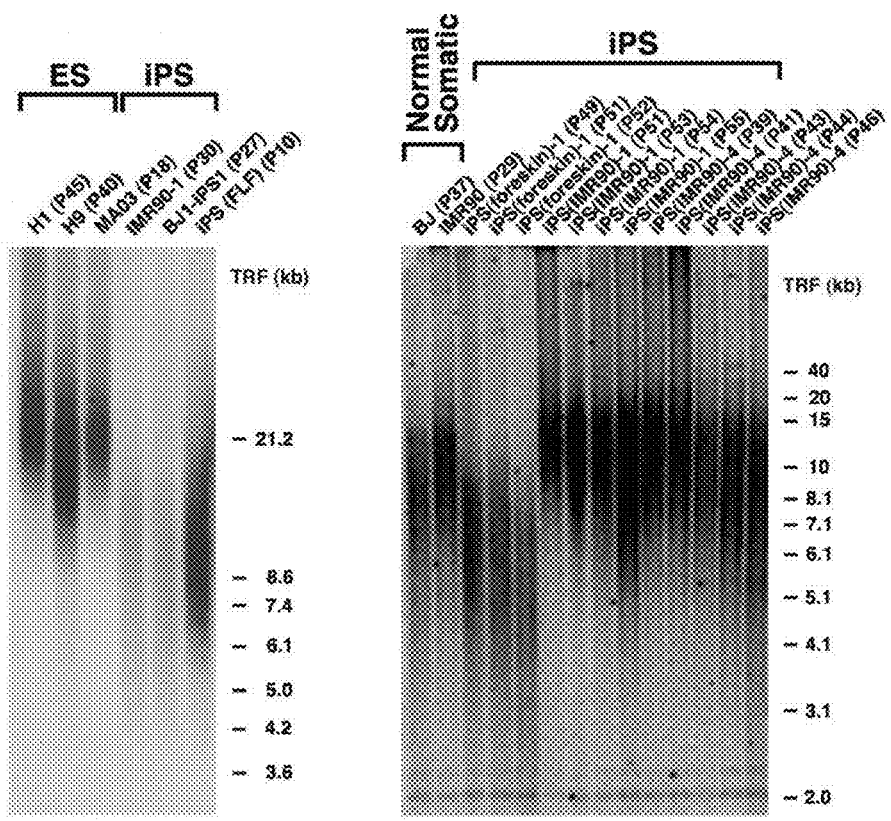
FIG. 1A and FIG. 1B. Relative TRF lengths in established human ES and iPS cell lines.

The terms "reference" and "control" are used interchangeably to refer to a known value or set of known values against which an observed value may be compared. As used herein, known means that the value represents an understood parameter, e.g., a level of expression of a marker gene in a graft survival or loss phenotype. A reference or control value may be from a single measurement or data point or may be a value calculated based on more than one measurement or data point (e.g., an average of many different measurements). Any convenient reference or control value(s) may be employed in practicing aspects of the subject invention.

The term "nucleic acid" includes DNA, RNA (double-stranded or single stranded), analogs (e.g., PNA or LNA molecules) and derivatives thereof. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "mRNA" means messenger RNA. An "oligonucleotide" generally refers to a nucleotide multimer of about 10 to 100 nucleotides in length, while a "polynucleotide" includes a nucleotide multimer having any number of nucleotides.

The terms "protein", "polypeptide", "peptide" and the like refer to a polymer of amino acids (an amino acid sequence) and does not refer to a specific length of the molecule. This term also refers to or includes any modifications of the polypeptide (e.g., post-translational), such as glycosylations, acetylations, phosphorylations and the like. Included within the definition are, for example, polypeptides containing one or more analogs of an amino acid, polypeptides with substituted linkages, as well as other modifications known in the art, both naturally occurring and non-naturally occurring.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

The terms "profile" and "signature" and "result" and "data", and the like, when used to describe peptide level or gene expression level data are used interchangeably (e.g., peptide signature/profile/result/data, gene expression signature/profile/result/data, etc.).

The terms "cells reprogrammed to pluripotency", "reprogrammed cell lines", "induced pluripotent stem cells", "iPS cells", "de-differentiated cells" and the like as used herein refer to pluripotent cells or pluripotent cell lines that have been generated from a non-pluripotent cell/cell line, e.g., an adult somatic cell, by artificial means, e.g., by the exogenous expression of certain pluripotency-inducing genes, somatic cell nuclear transfer, etc. (see, e.g., Takahashi K, Tanabe K, Ohnuki M, Narita M, Ichisaka T, Tomoda K, Yamanaka S. 2007 "Induction of pluripotent stem cells from adult human fibroblasts by defined factors" Cell 131: 861-72; and Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A 2007 "Induced pluripotent stem cell lines derived from human somatic cells" Science 318: 1917-1920; and PCT application publication WO/2007/019398 entitled "Improved Methods of Reprogramming Animal Somatic Cells"; all of which are incorporated herein by reference in their entirety). Cells reprogrammed to pluripotency can be from any source or species, including from human, non-human mammal, or other animal. In certain embodiments, the non-pluripotent cells used to generate or produce the reprogrammed pluripotent cells are normal animal cells, meaning that the cells are not derived from subjects having a particular disease, disorder or other pathologic condition, e.g., normal mammalian or normal human somatic cells. In some embodiments, the normal non-pluripotent cells employed to produce the reprogrammed pluripotent cells are genetically-modified, including deletions, insertions, point mutations, etc., introduced in any convenient manner.

By "restoring telomere length", "restoring near-embryonic telomere length", and the like, is meant restoring telomere length of a pluripotent stem cell to that of an embryonic or germ cell, including but not limited to the telomere length of inner cell mass cells, early passage embryonic stem cells (ES cells), or sperm cells (generally in the range of 12 to 16 kb or more telomere restriction fragment (TRF) length). In certain embodiments, restoring telomere length means restoring telomere length of a pluripotent stem cell to be equivalent to the telomere length of an autologous embryonic/germ cell, e.g., an early passage ES cell from which a pluripotent stem cell is derived.

DETAILED DESCRIPTION OF THE INVENTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, the generation of clinical-grade cell-based therapies from human embryonic stem cells or cells reprogrammed to pluripotency from somatic cells, requires stringent quality controls to insure that the cells have long enough telomeres and resulting cellular lifespan to be clinically useful, and normal gene expression and genomic integrity so as to insure cells with a desired and reproducible phenotype and to reduce the risk of the malignant transformation of cells. Assays useful in identifying human embryonic stem cell lines and pluripotent cells resulting from the transcriptional reprogramming of somatic cells that have embryonic telomere length are described as well as quality control assays for screening genomic integrity in cells expanded and banked for therapeutic use, as well as assays to identify cells capable of abnormal immortalization.

Aspects of the present invention include methods of selecting/identifying cell lines of pluripotent stem cells, e.g., induced pluripotent stem cells (iPS cells) derived by reprogramming somatic cells with transcription factors, capable of restoring near-embryonic telomere restriction fragment length. The pluripotent stem cells may be evaluated for telomere restriction fragment (TRF) length, telomerase activity and/or expression level of one or more genes selected from PCNA, CDC2, MSH2, ZNF146, TERF1 transcript variant 2, VENTX and PRKDC. Pluripotent stem cells having near-embryonic telomere length, telomerase activity and/or levels of expression of the one or more genes equivalent to embryonic/germ cells, e.g., embryonic stem cells, are identified as ones that are clinically useful (i.e., having proliferative capacity suitable for therapeutic purposes). Thus, in certain embodiments, the selected/identified pluripotent cell lines have, or are capable of restoring, telomere restriction fragment length to at least 12, 13, 14, 15, 16, 17, or 18 or more kb. Aspects of the present invention also include compositions of cells produced and selected by the subject methods and systems, kits and computer program products for performing the identification/selection methods.

Telomeres in Cells Reprogrammed to Pluripotency

The present application provides experimental evidence that cells reprogrammed to pluripotency (e.g., iPS cells) have significant heterogeneity with respect to telomerase activity and telomere length, which impacts their therapeutic and research use. In other words, cells and cells lines reprogrammed to pluripotency have varying potential to reset telomere length (e.g., back to ES cell lengths, e.g., from 12 to 18 kb mean telomere restriction fragment (TRF) length). iPS cells that have not restored telomere length (or have low telomerase activity) have reduced proliferative capacity and thus senesce prematurely. The heterogeneity of cells reprogrammed to pluripotency identified herein demonstrates that, in contrast to some reports (e.g., Suhr et al. 2009 "Telomere dynamics in human cells reprogrammed to pluripotency" PLoS One 4(12):e8124; and Agarwal et al. 2010 "Telomere elongation in induced pluripotent stem cells from dyskeratosis congenital patients" Nature. 2010 Feb. 17 [Epub ahead of print]), cells reprogrammed to pluripotency do not, as a general rule, turn on significant telomerase activity and restore telomere lengths, e.g., to levels seen in embryonic/germ cells from the same individual. Thus, the present application demonstrates that there is a need to assay reprogrammed cell lines for telomere length, telomerase activity and/or the expression of genes indicative of telomere restoration prior to employing it for use in research and therapy. In view of the finding that telomere length can be used to predict proliferative lifespan or somatic cells (Allsopp R C, et al., Proc Natl Acad Sci USA. 1992 Nov. 1; 89(21):10114-8), this quality control step ensures that differentiated cell lineages derived from such reprogrammed pluripotent stem cells have a proliferative lifespan amenable for scale up and/or clinical use.

Methods and Compositions

Aspects of the present invention include methods of identifying pluripotent stem cells having proliferative capacity (or proliferation profiles) similar to embryonic cells (e.g., ES cells). In such aspects, the methods include identifying and/or selecting pluripotent stem cells that have respired or are capable of restoring telomere length to embryonic/germ cell levels.

In certain embodiment, the method includes evaluating the telomere length in a pluripotent stem cell and identifying the pluripotent stem cell as having embryonic proliferation capacity based on the telomere length. In certain embodiments, the method includes comparing the evaluated telomere length of the pluripotent stem cell with that of an embryonic or germ cell, where when telomere lengths of the pluripotent stem cell are similar to the embryonic or germ cell, the pluripotent stem cell is identified as having embryonic proliferation capacity. In certain embodiments, the evaluated telomere length of the pluripotent stem cell is compared to an autologous embryonic or germ cell, i.e., an embryonic/germ cell derived from the same individual. In certain of these embodiments, the autologous embryonic cell is an early passage of the embryonic stem cell from which the pluripotent stem cell was derived.

In certain embodiment, a pluripotent stem cell is identified as having embryonic proliferative capacity when the evaluated telomere length is at embryonic or near embryonic length, which is about 12 kb to about 16 kb or greater.

In practicing the methods, one or more distinct pluripotent stem cell may be analyzed at a time. For example, multiple different clonal reprogrammed cell lines (e.g., iPS cells) derived from the same parental cell may be analyzed for proliferative capacity as described herein. From these reprogrammed cell lines, those that have restored their telomeres, or are identified as having the capacity to do so, are identified and/or selected as having embryonic or near-embryonic proliferation capacity. The number of distinct reprogrammed cell lines/clones analyzed can vary, including 2, 3, 4, 5, 6, 7, 8, 9, 10, 20, 30, 50, 100, or more reprogrammed cell lines/clones. In the event that one or more reprogrammed cell line is identified as not having restored telomere length, such reprogrammed cell lines can be passaged further and assayed at a later time point (see, e.g., iPS line EH3 in FIG. 8, described in detail below). Thus, screening a reprogrammed cell line for proliferative capacity as described herein may take place at multiple different time points during the propagation of a reprogrammed cell line. A reprogrammed cell line may thus be identified in an early passage as not having restored telomere length while at a later passage being identified as having restored telomere length.

In certain embodiments, pluripotent stem cells having embryonic proliferation capacity are identified/selected by evaluating the expression level of at least one gene in the pluripotent stem cells to obtain a gene expression level result, wherein the at least one gene is selected from one or more of: PCNA, CDC2, MSH2, ZNF146, TERF1 transcript variant 2, VENTX and PRKDC; and identifying the pluripotent stem cells as capable of restoring telomere restriction fragment length based on the gene expression level result.

In certain embodiments, the gene expression evaluation level result is a protein expression level result. In certain embodiments, the gene expression evaluation level result is a nucleic acid expression level result. Any convenient method for evaluating gene expression can be employed. Gene expression evaluation may be qualitative or quantitative. As such, where detection is qualitative, the methods provide a reading or evaluation, e.g., assessment, of whether or not the target analyte, e.g., peptide, nucleic acid or other expression product (e.g., protein), is present in the sample being assayed. In yet other embodiments, the methods provide a quantitative detection of whether the target analyte is present in the sample being assayed, i.e., an evaluation or assessment of the actual amount or relative abundance of the target analyte, e.g., peptide or nucleic acid in the sample being assayed. In such embodiments, the quantitative detection may be absolute or, if the method is a method of detecting two or more different analytes in a sample, relative. As such, the term "quantifying" when used in the context of quantifying a target analyte in a sample can refer to absolute or to relative quantification. Absolute quantification may be accomplished by inclusion of known concentration(s) of one or more control analytes and referencing the detected level of the target analyte(s) with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other. In addition, a relative quantitation may be ascertained using a control, or reference, sample (e.g., as is commonly done in array based assays as well as in quantitative PCR/RT-PCR analyses or sequencing and analysis of the transcriptome).

Thus, in certain embodiments, the evaluating step comprises comparing the gene expression result to a reference gene expression result. In certain embodiments, the reference gene expression result is from embryonic stem cells where the expression of the at least one gene in the pluripotent stem cells is similar or equivalent to the expression of the at least one gene in the embryonic stem cells. Where the expression of multiple genes is assessed, the pattern of gene expression for the multiple genes can be compared to the pattern of expression of the same genes in a reference gene expression result (e.g., from an embryonic stem cell line). In certain embodiments, the embryonic stem cells are human embryonic stem cells with telomere restriction fragment (TRF) lengths of 12 to 18 kilobases (kb). In certain embodiments, the pluripotent stem cells are cells are capable of restoring telomere restriction fragment length to 12 to 18 kb. In certain embodiments, the pluripotent stem cells are cells that have been reprogrammed to become pluripotent stem cells, also called induced pluripotent stem cells (iPS cells). In certain embodiments, the iPS cells are derived by reprogramming somatic cells with at least one gene or gene product (e.g., nucleic acid or protein) selected from one or more of: transcription factors SOX2, OCT4 and KLF4. In certain embodiments, the pluripotent cells display a normal karyotype. In certain embodiments, the at least one gene or gene product further includes: SIRT1, PARP1, BLM, TRF1, POT1, RPA1, RPA2, RPA3, MSH2, MSH6, CDC2, CHEK1, CHEK2, BRCA1, L1TD1, EXO1, SMC2L1, RFC2, KPNA2, MAD2L2, HELLS, DKC1, POU2F1, PLK1, CDT1, LMNB1, PRKDC, PIN1, SYNE1, TERF2IP and LMNA.

Aspects of the present invention include methods of identifying pluripotent stem cells capable of restoring telomere length including:

evaluating telomerase activity in the pluripotent stem cells to obtain a telomerase activity result; and identifying the pluripotent stem cells as capable of restoring telomere restriction fragment length based on the telomerase activity result.

In certain embodiments, the pluripotent stem cell (or pluripotent stem cell line) is evaluated for telomerase activity by determining the activity of telomerase and/or by determining telomere length at different passages in culture (i.e., at least two passages). In such embodiments, a pluripotent stem cell is identified as being capable of restoring telomere restriction fragment length when the evaluated telomerase activity/length at a later passage is increased as compared to the evaluated telomerase activity/length at an earlier passage. For example, if the telomere length of passage 10 is increased as compared to the telomere length of passage 3 of a pluripotent stem cell line (e.g., an iPS cell line), then the pluripotent stem cell line is capable of restoring telomere restriction fragment length. Telomere length may be evaluated in three or more passages, where the pluripotent stem cell line is identified as capable of restoring telomere length when the evaluated telomere length in each later passage is longer than the evaluated telomere length in each earlier passage. The number of passages of a pluripotent stem cell evaluated can vary, and can include from 2 to 30 passages, including 2 or more, 3 or more, 4 or more, 5 or more, 7 or more, 10 or more, 15 or more 20 or more, 25 or more, etc. A pluripotent stem cell may be evaluated at regular intervals of serial passages (e.g., every passage, every 2 passages, every 3 passage, every 4 passages, etc.) or at irregular intervals of serial passages as desired by the user.

Evaluation of telomerase activity and/or length may be accomplished using any convenient method, and as such, no limitation in this regard is intended. For example, telomere length can be determined by: Southern blot analysis assay using telomere-specific probe; fluorescence in-situ hybridization (FISH); hybridization protection assay; PCR-based methods (e.g., quantitative PCR), including single telomere length analysis (STELA) (see, e.g., Baird et al., Nature Genetics vol 33, pp. 203-207 "Extensive allelic variation and ultrashort telomeres in senescent human cells", incorporated herein by reference); flow cytometry based methods (see, e.g., Lauzon et al., Cytometry. 2000 Jun. 15; 42(3): 159-64 "Flow cytometric measurement of telomere length", incorporated herein by reference); and Flow-FISH telomere assays (see, e.g., Baerlocher et al. Nat Protoc 2006; 1:2365-2376 "Flow cytometry and FISH to measure the average length of telomeres (flow FISH)", incorporated herein by reference). Exemplary telomerase activity assays include, but are not limited to: gene expression assays (e.g., for TERT or other genes associated with telomoerase activity, e.g., as described herein); flow cytometric assays for TERT (see, e.g., Handaa et al., Leukemia Research, Volume 34, Issue 2, Pages 177-183 "Flow cytometric detection of human telomerase reverse transcriptase (hTERT) expression in a subpopulation of bone marrow cells", incorporated herein by reference); telomere repeat amplification protocol (TRAP) (see, e.g., Fajkus, Clin Chim Acta. 2006 September; 371(1-2):25-31 "Detection of telomerase activity by the TRAP assay and its variants and alternatives", incorporated herein by reference).

the pluripotent cell line is further identified as capable of restoring embryonic stem cell telomere length when said evaluated telomere length of said later passage is at least 12 kb.

In certain embodiments, a pluripotent cell line may be identified as capable of restoring embryonic stem cell telomere length, for example when the evaluated telomere length of a passage is at least 12 kb, at least 13 kb, at least 14 kb, at least 15 kb, at least 16 kb, at least 17 kb, at least 18 kb, etc. In certain embodiments, evaluated telomere length is compared to cells or cell lines (e.g., ES cell lines) known to have embryonic stem cell telomere length.

In certain embodiments, the evaluating step further includes evaluating expression level of at least one gene in the pluripotent stem cells to obtain a gene expression level result, wherein the at least one gene is selected from one or more of: PCNA, CDC2, MSH2, ZNF146, TERF1 transcript variant 2, VENTX and PRKDC; and the identifying step further includes identifying the pluripotent stem cells as capable of restoring telomere restriction fragment length based on the gene expression level result.

Aspects of the present invention further include methods to increase or decrease telomere length in cells reprogrammed to pluripotency. For example, reprogrammed cells can be treated with agents that regulate the phosphorylation of the telomere-binding factor TRF1 (Terf1), which negatively regulates telomere length by inhibiting access of telomerase at telomere termini. Casein kinase 2 (CK2)-mediated phosphorylation of TRF1 is required for efficient telomere binding. Thus, inhibition of CK2 activity will result in a reduction in TRF1 telomere binding to telomeres and allow telomerase access to, and elongation of, telomeres. The CK2 inhibitor 5,6-dichloro-1-beta-d-ribofuranosylbenzimidazole (DRB, Calbiochem) has been shown to decreased the ability of TRF1 to bind telomeric DNA (Kim et al. J Biol Chem. 2008 May 16; 283(20):14144-52 "Regulation of telomeric repeat binding factor 1 binding to telomeres by casein kinase 2-mediated phosphorylation", incorporated herein by reference). This report also showed that partial knockdown of CK2 by small interfering RNA also resulted in release of TRF1 from telomeres. In both cases, the released TRF1 was ubiquinated and degraded. Conversely, activation of CK2 activity will result in an increase in TRF1 telomere binding to telomeres and prevent telomerase access to, and elongation of, telomeres (thus resulting in shortening of telomeres during propagation of the cells).

In certain other embodiments, increasing telomere length in cells reprogrammed to pluripotency includes administering exogenous VENTX to the cells. Administration can be achieved in any convenient manner. For example, VENTX can be present in an expression vector operably linked to promoter/transcriptional regulatory sequences that drive expression in the reprogrammed cells (e.g., plasmid vector, viral vector, and the like) and transfected/transduced into the cells. Promoters/transcriptional regulatory sequences may be constitutively active, active at certain developmental stages, or inducible (e.g., using inducing agents in culture, e.g., tetracycline/doxycycline, ecdysone, inducers of endogenous transcription factors, etc.). No limitation in this regard is intended. As another example, VENTX may be provided to the reprogrammed cell as a protein, e.g., transfected into the reprogrammed cells or provided in the cell culture in a form that can be taken into the cells (e.g., having cell permeable peptide/protein translocation domains, e.g., HIV TAT-based domain, poly arginine, Antennapedia third α-helix domain, etc.).

Aspects of the present invention include induced pluripotent stem cells (iPS cells) identified according to the methods described herein.

Aspects of the present invention include induced pluripotent stem cell (iPS cell) comprising a telomere restriction fragment length of from 12 to 18 kb. In certain embodiments, the telomere restriction fragment length is at least 15 kb. In certain embodiments, the iPS cell displays a normal karyotype.

Reprogrammed cells according to the present invention can be used in a variety of research and therapeutic settings. For example, reprogrammed cells (e.g., iPS cells) with restored embryonic telomere length can be used to generate "young" progenitor cell lines, including clonal or oligoclonal progenitor cell lines (e.g., as described in PCT application publication WO/2007/062198 entitled "Methods to Accelerate the Isolation of Novel Cell Strains from Pluripotent Stem Cells and Cells Obtained Thereby", incorporated herein by reference). By "young" progenitor cell lines is meant that the progenitor cell lines produced have a telomere length, and thus an expected life span, similar to corresponding tissue from young animals (e.g., as compared to animal s reaching the end of their normal life-span).

iPS or similar pluripotent stem cells made by reprogramming somatic cells (for example as described in US Patent Publication No. 2010/0167404 titled "Methods of Reprogramming Animal Somatic Cells", incorporated herein by reference), can be used to create somatic cell types for cellular therapies. The surprising observation described herein that transcriptional reprogramming does not normally reset embryonic telomere length to aged somatic cells, in contrast to the telomere restoration seen in somatic cell nuclear transfer, makes it important to implement the methods described herein as a quality control step in making cell-based therapies from such reprogrammed cells. We demonstrate how cells that have successfully reset embryonic telomere length can be identified, selected, and used in clinical applications where an extension of cell lifespan is desirable, e.g., in industrial scale up of master and working cell banks and generating large quantities of products for the treatment of age-related degenerative diseases, including but not limited to: retinal pigment epithelial cells for treating age-related macular degeneration; vascular progenitors for age-related vascular dysfunction including coronary artery disease, hypertension, heart failure, and stroke; blood stem cells and blood progenitors for treating immune senescence; osteoprogenitors for osteoporosis; hepatocytes for cirrhosis; myoblasts for muscle wasting; and so on.

In one example, young hemangioblasts (precursors of both blood and circulating vascular progenitors) produced from reprogrammed cells identified according to aspects of the subject invention find use in the repair of age-related endothelial dysfunction (such as occurs in atherosclerosis, hypertension, or Alzheimer's disease. Young hemangioblasts/hematopoietic stem cells further find us in the reconstitution of young, proliferation competent blood cells to aged patients or patients with premature aging of blood cell types, such as in the case of chronic HIV, CMV, and herpes zoster virus infection.

Given the high therapeutic value of such young progenitor cell lines, aspects of the present invention include evaluating telomere length in cells derived from a subject (e.g., in one or more tissues of interest in an animal, including a mammal, e.g., a human subject) and treating those subjects having shortened telomeres with young progenitor cells corresponding to the identity of the cells/tissue evaluated. The threshold length of telomeres considered "short" and thus indicating that the subject is a candidate for progenitor cell therapy is below a threshold level. In certain embodiments, the threshold level is set at the lower quartile (i.e., the $25^{th}$ percentile) or less of telomere length of the same cells in healthy control subjects or subjects, where the control subjects may be at the same or younger age than the subject. The threshold level may thus be the lower tenth percentile, the lower fifth percentile, the lower first percentile, etc. In certain embodiments, the threshold telomere length is set at a telomere restriction fragment (TRF) length, where in certain embodiments the threshold TRF length is 6 kb or less, including 4 kb or less, 2 kb or less, and 1 kb or less, etc. Telomere length evaluation can be accomplished in any convenient manner, e.g., as described above (e.g., by Southern blot, flow-FISH, STELA, etc.). As one example (as noted above), subjects having shortened telomeres in blood and/or vascular cells can be treated with young hemangioblasts and/or hematopoietic progenitor cells.

Aspects of the present invention include kits that contain: reagents for evaluating the expression level of the genes PCNA, CDC2, MSH2, ZNF146, VENTX and PRKDC.

Aspects of the present invention include systems for identifying a pluripotent stem cell capable of capable of restoring telomere length including:

a gene expression level evaluation element configured for evaluating the level of expression of at least one gene in a pluripotent stem cell to obtain a gene expression level result, wherein the at least one gene is selected from one or more of: PCNA, CDC2, MSH2, ZNF146, VENTX and PRKDC; and a phenotype determination element configured for employing the gene expression level result to identify a pluripotent stem cell capable of capable of restoring telomere length.

In certain embodiments, the phenotype determination element comprises a reference gene expression level result. In certain embodiments, the reference gene expression level result is from embryonic stem cells. In certain embodiments, the embryonic stem cells are human embryonic stem cells with telomere restriction fragment lengths of 12 to 18 kilobases (kb).

The subject systems and kits may also include one or more other reagents for preparing or processing samples or cells according to the subject methods. The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps for producing a normalized sample according to the present invention.

In addition to above-mentioned components, the subject kits typically further include instructions for using the components of the kit to practice the subject methods, e.g., to prepare nucleic acid samples for perform the mutation process according to aspects of the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control samples and reagents, e.g., two or more control samples for use in testing the kit.

Also provided are databases of peptide signatures and/or gene expression profiles of pluripotent stem cells capable of restoring telomere restriction fragment length. The peptide signatures and/or gene expression profiles and databases thereof may be provided in a variety of media to facilitate their use (e.g., in a user-accessible/readable format). "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user. One format for an output means ranks expression profiles possessing varying degrees of similarity to a reference expression profile. Such presentation provides a skilled artisan (or user) with a ranking of similarities and identifies the degree of similarity contained in the test expression profile to one or more references profile(s).

As such, the subject invention further includes a computer program product for identifying a pluripotent stem cell (e.g., and iPS cell) as one that is capable of restoring telomere restriction fragment length. The computer program product, when loaded onto a computer, is configured to employ a gene expression level result (protein and/or nucleic acid) of a pluripotent stem cell to make this determination. Once determined, the telomere restriction fragment length restoration capability of the pluripotent cell is provided to a user in a user-readable format. In addition, the computer program product may include one or more reference or control peptide and/or gene expression signatures (as described in detail above) which are employed to determine the clinical transplant category of the patient.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Telomere length regulation is important for maintenance of the immortal phenotype of reproductive-lineage cells and for setting the replicative lifespan of mortal somatic cells. While transcriptional reprogramming is capable of reversing the differentiation of somatic cells to induced pluripotent stem cells, such reprogramming may not reverse cellular aging by the restoration of embryonic telomere lengths. Indeed, Feng et al. (Stem Cells, 28(4):704-12) describe that, in contrast to hES cell derivatives, hemangioblasts/blast cells and RPE generated from human iPS cells displayed limited expansion capability and exhibited apoptosis morphology, stating that the underlying molecular mechanisms for these differences remain elusive. We therefore surveyed telomere length in widely-distributed hES and iPS cell lines and observed variable but relatively long TRF lengths in three hES cell lines (16.09-21.1 kb) but markedly shorter TRF lengths (6-10.2 kb) in five iPS cell lines. Transcriptome analysis comparing hES and iPS cell lines showed only modest variation in a small subset genes implicated in telomere length regulation. However, iPS cell lines consistently showed reduced levels of telomerase activity by TRAP assay compared to hES cell lines. To reduce genotypic variation in TRF lengths and provide a more reproducible system for studying telomere dynamics during reprogramming, we utilized the isogenic background of a characterized hES-derived clonal embryonic progenitor line designated EN13 as a substrate for reprogramming. The EN13-derived isogenic iPS cell clones showed initial telomere lengths comparable to EN13, had telomerase activity, expressed ES cell markers and a telomere-related transcriptome similar to hES cells. Subsequent culture of the lines generally showed telomere shortening to lengths similar to that observed in the widely-distributed iPS lines. However, the selection of an EN13-derived iPS colony for relatively high telomerase activity led to a line designated EH3 with progressively increasing TRF length over 60 days of propagation, eventually returning the embryonic lengths of hES cells. We conclude that the use of markers for robust telomere length regulation after transcriptional reprogramming can result in the reversal of developmental aging and could have important implications for the development of future therapies for age-related degenerative disease.

Figure 1B:
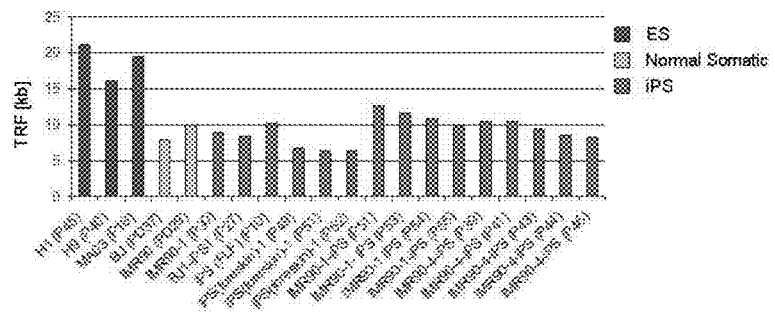

Results
Survey of Telomere Dynamics and Telomere-Related Gene Expression in Established Human ES and iPS Cell Lines We cultured three characterized hES cell lines H1(WA01), H9(WA09) (Thomson J A et al, 1998) and ACT03(MA03) (Lund R D et al, 2006) and five widely-disseminated iPS lines: IMR90-1 (Takahashi et al, 2007), iPS (IMR90)-1 (P30); iPS(IMR90)-4; and iPS(foreskin)-1 (Yu, J. et al, 2007), BJ1-iPS1 (Park I H et al, 2008), and one iPS cell line designated iPS(FLF) previously produced by one of us (IS) and not widely distributed (unpublished)), and assessed TRF length by Southern blot (FIG. 1). We observed variable but relatively long TRF lengths in hES cell lines of 16.09-21.1 kb, but markedly shorter TRF lengths ranging from 6-10.2 kb in all of the iPS cell lines studied. In the case of those lines we serially passaged (iPS (IMR90)-1 (P30); iPS (IMR90)-4; and iPS(foreskin)-1), TRF length progressively shortened during propagation in vitro. Particularly striking was the near-senescent TRF length of iPS(foreskin)-1 which showed a critical TRF length of approximately 6 kb at P52.

Figure 2A:
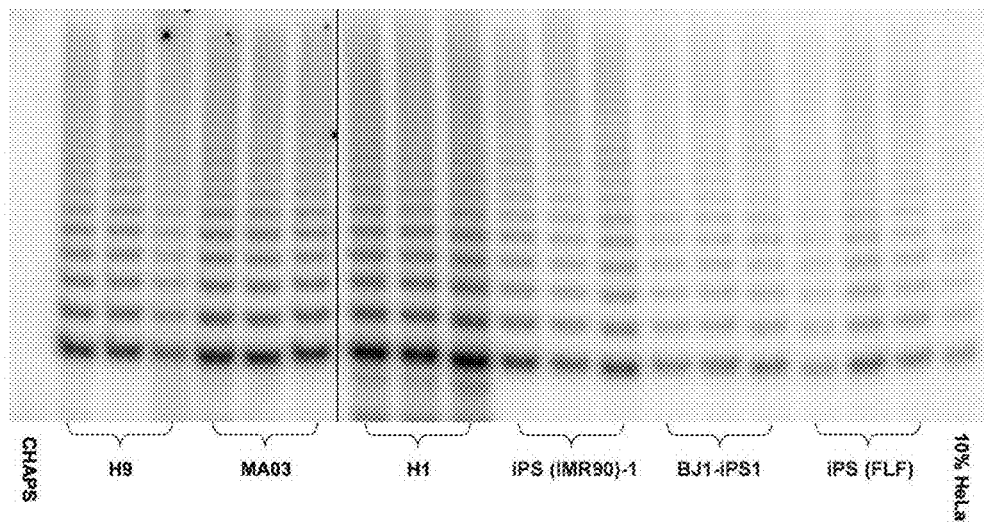
FIG. 2A and FIG. 2B. TRAP assays of relative telomerase activity in human ES and iPS cell lines.
Figure 2B:
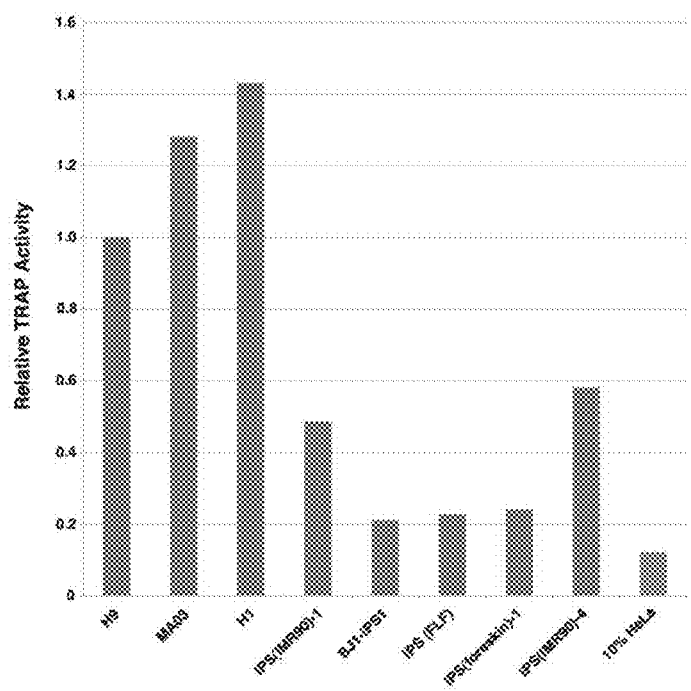

We have previously shown that telomerase activity is a stem cell biomarker in fetal and adult hematopoietic cells (Chiu et al, 1996). Telomerase activity is also present in preimplantation embryos of many species and also in hES cells (Mantell et al, 1994; Schaetzlein et al, 2004; Wright, et al, 1996). To investigate possible causes of the shortened telomeres in iPS cell lines, we therefore measured telomerase activity in a panel of hES and iPS cells via Telomere Repeat Amplification Protocol (TRAP) assay normalized by total protein loaded (Kim et al, 1994). As seen in FIG. 2a, all hES and iPS cell lines showed telomerase activity, though iPS cell lines displayed lesser activity than hES cell lines (quantification of the bands is shown in FIG. 2b).

Figure 3:
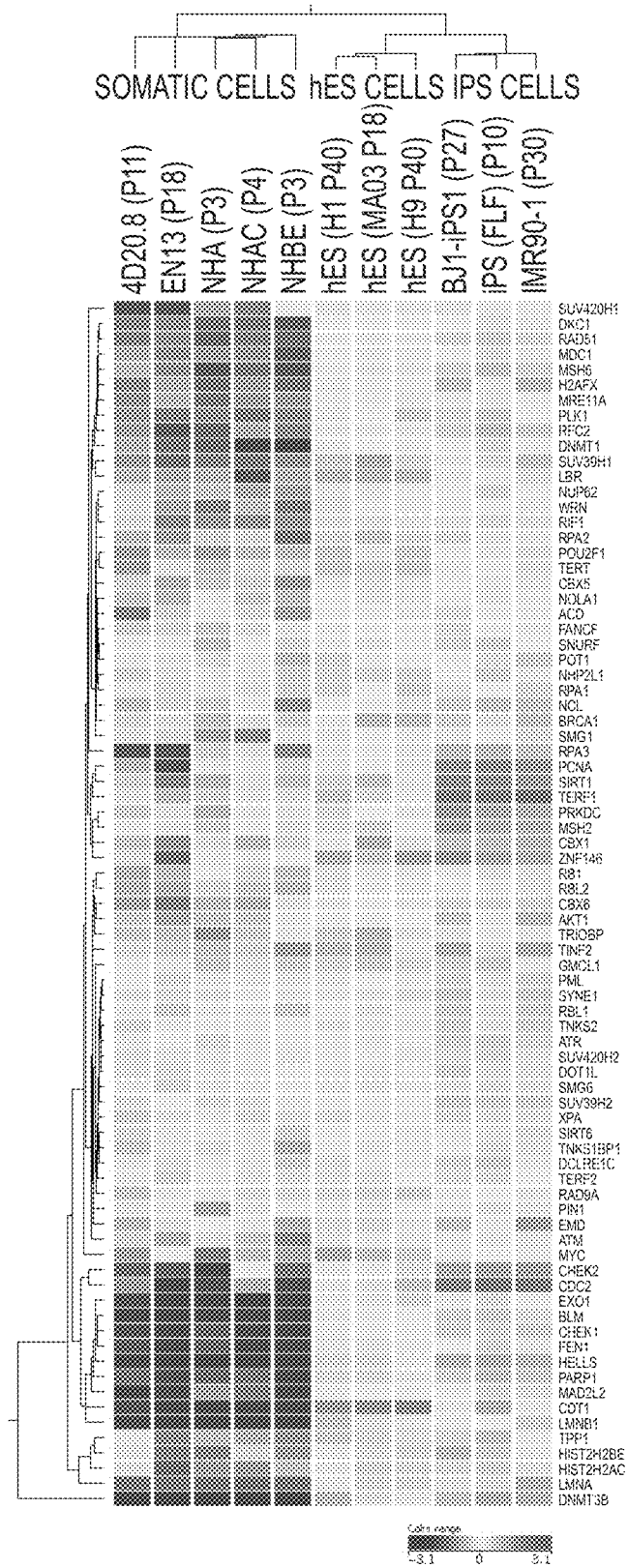
FIG. 3. Heat map of telomere-related genes in established human ES and iPS cell lines compared to the somatic cells. Human H9-derived clonal embryonic progenitors 4D20.8 and EN13 along with representatives of the three germ layers (normal human astrocytes (NHA), normal human articular chondrocytes (NHAC), and normal human bronchial epithelium (NHBE) are compared to three human ES and iPS cell lines. The heat map includes genes associated with telomere length regulation and include multiple splice variants. Genes are clustered in the vertical axis by similar expression pattern in the lines. Color key shows logfold differences in expression (red being high, blue low).

Numerous genes have been implicated in the complex system regulating telomere length, including those for the telosome (shelterin) complex such as TERF1(TRF1), TERF2(TRF2), TINF2(TIN2), TERF2IP(RAP1), ACD (TPP1), genes encoding methyltransferases implicated in the methylation of subtelomeric sequences such as DNMT3b (Gonzalo S et al, 2006), those involved in recombination such as the BLM, HELLS and WRN helicases (the latter mutated in the premature aging syndrome Werner syndrome), genes implicated in the alternative lengthening of telomeres (ALT) pathway such as MSH2, nuclear lamina proteins such as LMNA and LMNB1 (mutations in the former being the cause of the premature aging disorder progeria (Hutchinson-Gilford syndrome), members of the MRE11 complex such as MRE11A, NBS1, and RAD50, the telomerase catalytic component TERT, as well as additional genes. We measured relative levels of these telomere-related transcripts in mRNA from three hES cell lines, normal human astrocytes, bronchial epithelia, and articular chondrocytes (representing adult derivatives of ectoderm, endoderm, and mesoderm respectively), the two EP cell lines 4D20.8 and EN13, and the three iPS cell lines described above. Transcripts were analyzed utilizing Illumina microarrays. In FIG. 3 we summarize the gene expression data in a heat map (numerical values available in Supplementary Table I). Interestingly, striking differences in numerous telomere-related genes other than the well-documented up-regulation of TERT were observed between hES and the differentiated cells analyzed. Genes up-regulated in hES cells included: SIRT1, PARP1, BLM, TRF1, POT1, RPA1, RPA2, RPA3, MSH2, MSH6, CDC2, CHEK1, CHEK2, BRCA1, L1TD1, EXO1, SMC2L1, RFC2, KPNA2, MAD2L2, HELLS, DKC1, POU2F1, PLK1, CDT1, LMNB1, and PRKDC. Genes up-regulated in differentiated cells compared to hES and iPS cells included PIN1, SYNE1, TERF2IP, LMNA. These differences between hES cells and differentiated cells extended to >100 differentiated cell types we have assayed (data not shown).

Significantly, minor differences were also observed in the sampled hES and iPS cell lines (FIG. 3). All three iPS lines analyzed by microarray showed higher levels of KPNA2, encoding a nuclear protein involved in the transport of NBS1 and OCT4 (Li X et al, 2008) than the hES cells assayed. Also elevated in the iPS lines relative to hES were MSH2, CDC2, ZNF146, PCNA, and PRKDC.

Re-Derivation of H9-Like Cells (ReH9) from H9-Derived Clonal Embryonic Progenitors by Induced Pluripotency The large variability in the subtelomeric region in differing genotypes (Levy et al, 1992) complicates precise comparisons of TRF values in reprogrammed cells and normal hES cell lines. Therefore, to determine whether transcriptional reprogramming can reverse cellular aging and restore embryonic telomere length to differentiated cells that have undergone aging, we utilized clonally-purified mortal progenitors with characterized telomere length and replicative lifespan (West et al, 2008). We expressed the reprogramming factors SOX2, OCT4, and KLF4 (Takahashi et al, 2007) in the human embryonic progenitor cell line EN13 (P13), a line with differentiated markers of splanchnopleuric mesoderm. EN13 is a mortal telomerase (−) line with a maximum replicative lifespan of approximately 80 PDs.

Figure 4:
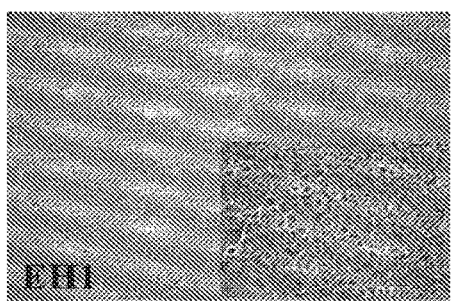
FIG. 4. Phase contrast photographs of ReH9 iPS clones. Each ReH9 iPS cell clone is shown at reduced and high magnification by phase contrast. All iPS cell lines shown showed similar phenotypes in feeder-free conditions. The cells were small round cells with large nucleoli and large nuclear/cytoplamic ratios typical of hES cells under the same conditions.
Figure 4:
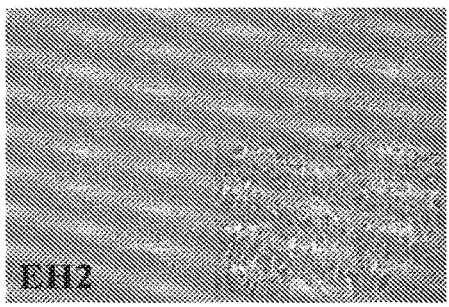
Figure 4:
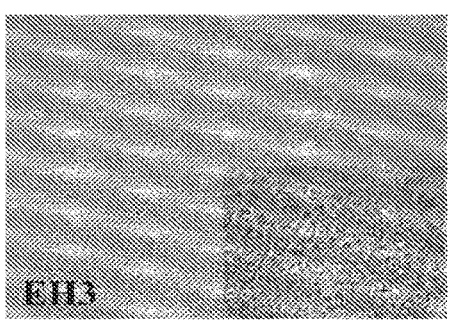
Figure 4:
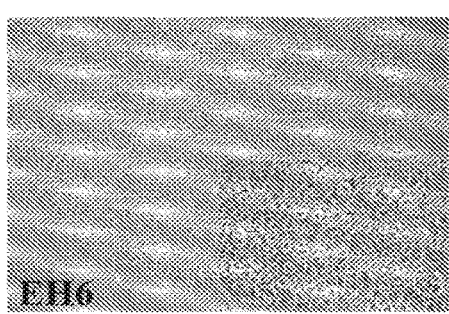
Figure 4:
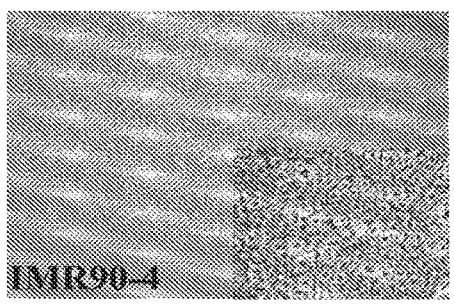
Figure 4:
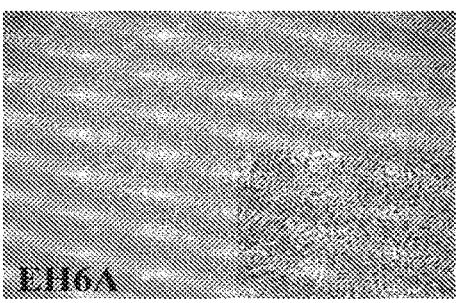
Figure 4:
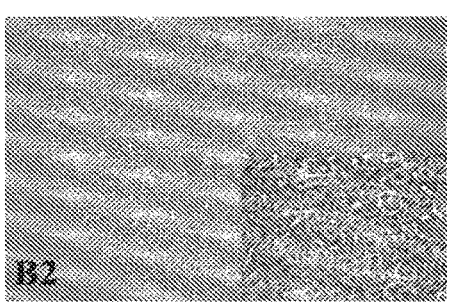
Figure 4:
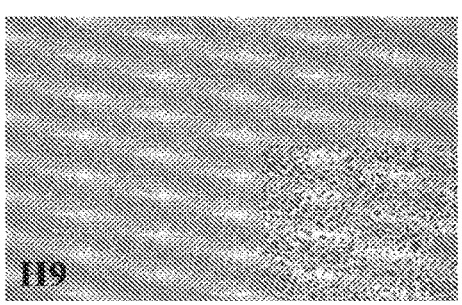

The established ReH9 colonies had morphological characteristics of human pluripotent stem cells that included large nuclear/cytoplasmic ratios, small and tightly packed, distinct nucleoli and well-defined boundaries on feeders (FIG. 4). We established six independent clones and cultured them long term under feeder free conditions using mTeSR1 media system containing 100 ng/ml bFGF to prevent inaccurate TRF measurements as a result of contaminating ultra-long mouse telomeres.

Figure 5:
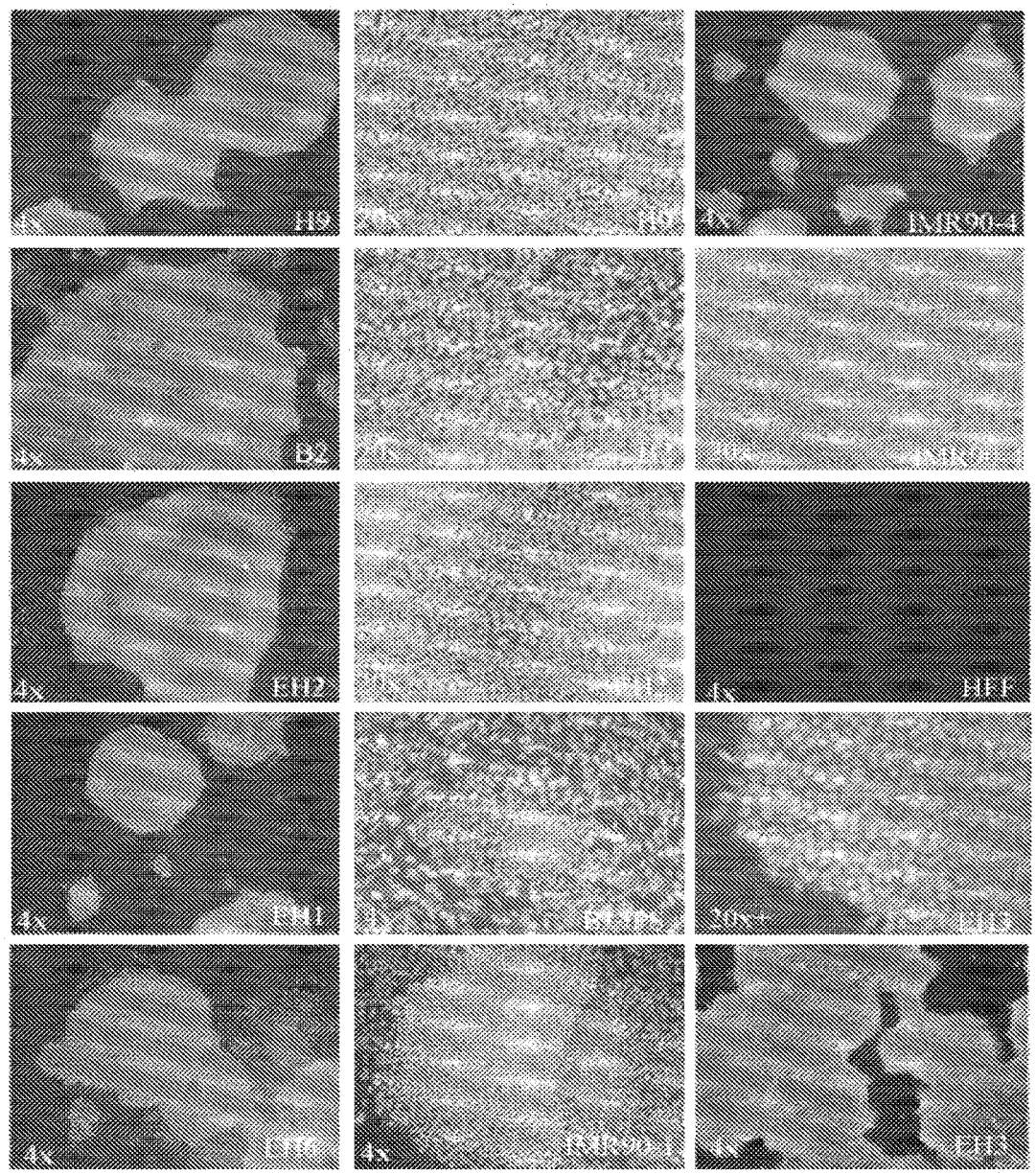
FIG. 5. Immunofluorescence photographs of hES and EN13-iPS clones. Immunohistochemical staining for Oct4 in H9 hES cells and ReH9 cell lines at varying magnifications. Primary antibody is monoclonal mouse antibody against human Oct4. Secondary goat anti-mouse fluorescein conjugated antibody was used to detect the signal. Isotype antibody controls gave no specific signal.
Figure 12:
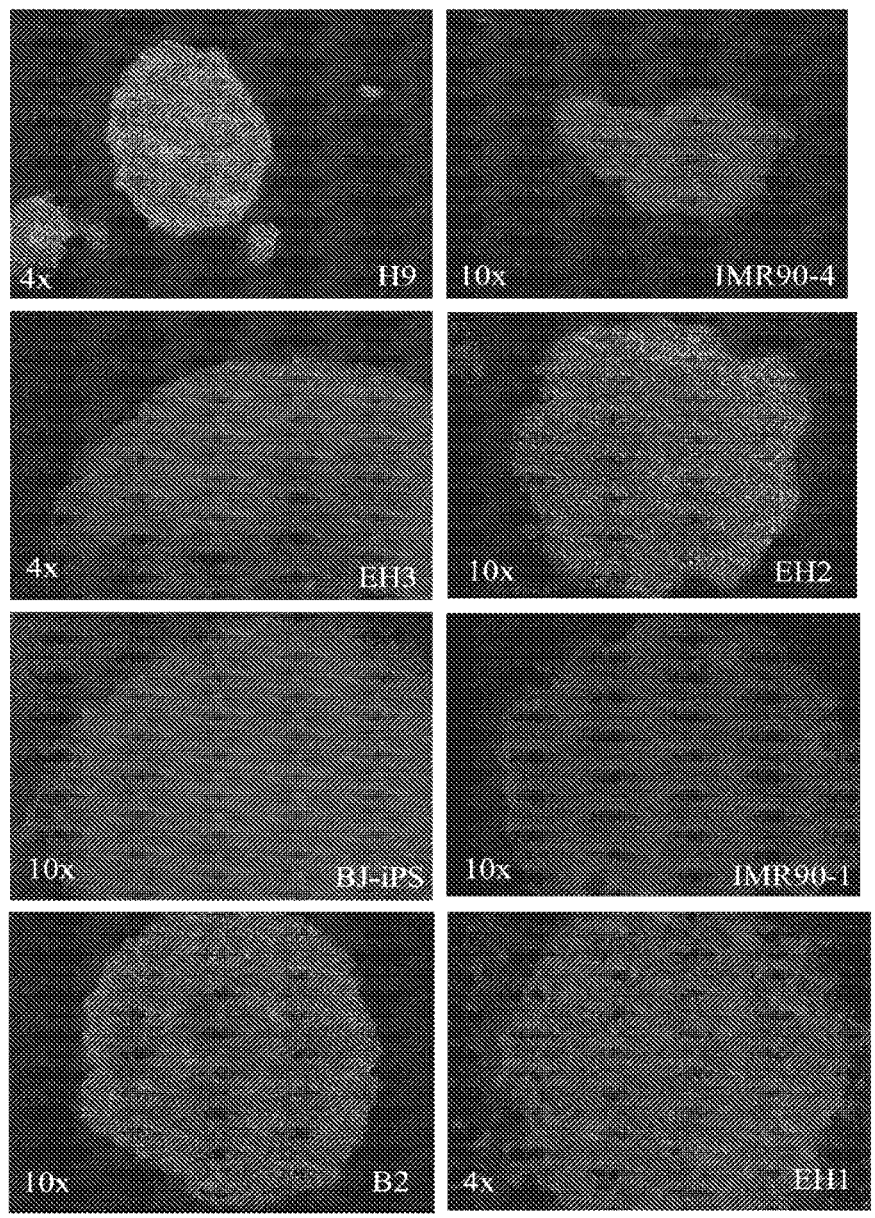
FIG. 12. Alkaline phosphatase activity in RH9 and control hES and iPS lines. Colonies were grown on chamber slides coated with matrigel and stained using an alkaline phosphatase detection kit.
Figure 13:
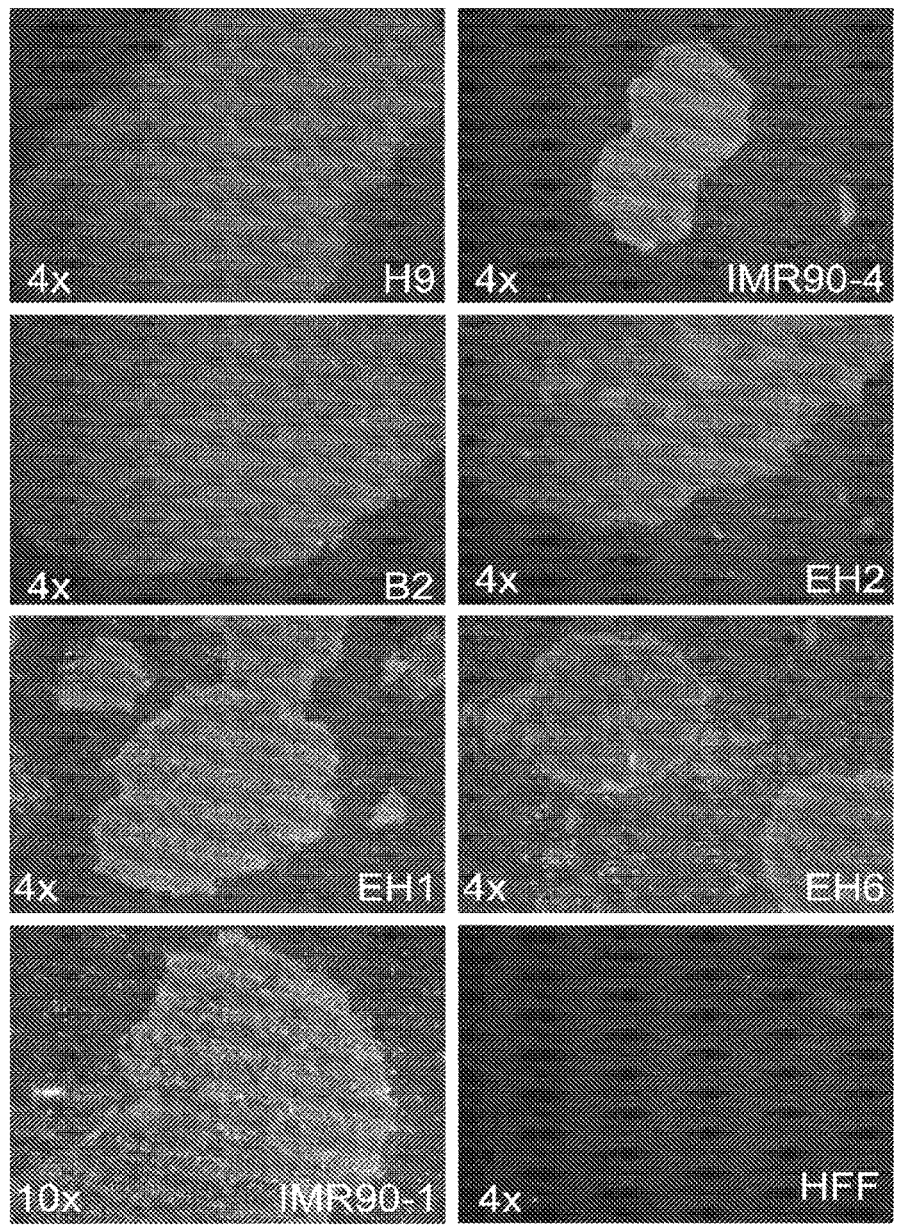
FIG. 13. Immunohistochemical staining of RH9 cell lines with an SSEA4 antibody. The cells were grown as before on chamber slides, fixed and the SSEA4 protein was detected using a mouse monoclonal antibody against SSEA4. A secondary goat anti-mouse fluorescein conjugated antibody was used to detect the signal.

The designated ReH9 cell lines, EH1, EH2, EH3, EH6, EH6A and B2 were then assayed for the expression of markers characteristic of hES cells. As shown in FIG. 5, all lines showed bright Oct4 staining not observed in the presence of isotype antibody or in control differentiated cells. All ReH9 clones also stained for other pluripotency markers such as alkaline phosphatase (FIG. 12) and specific staining for SSEA4 (FIG. 13).

Figure 6A:
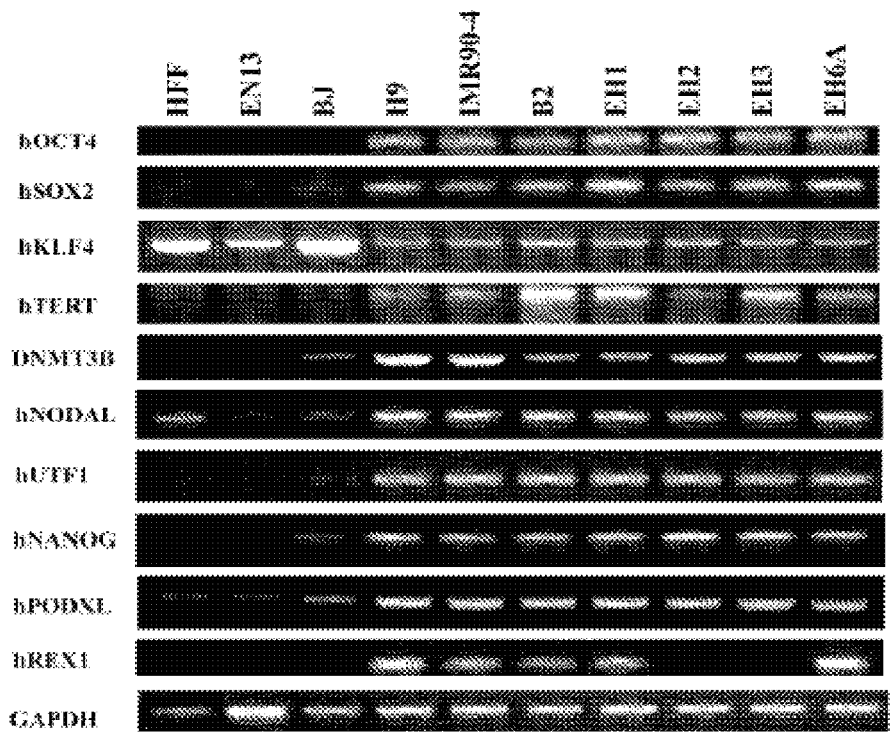
FIG. 6A and FIG. 6B. Analysis of pluripotency factors in ReH9 cells by RT-PCR analysis.
Figure 6B:
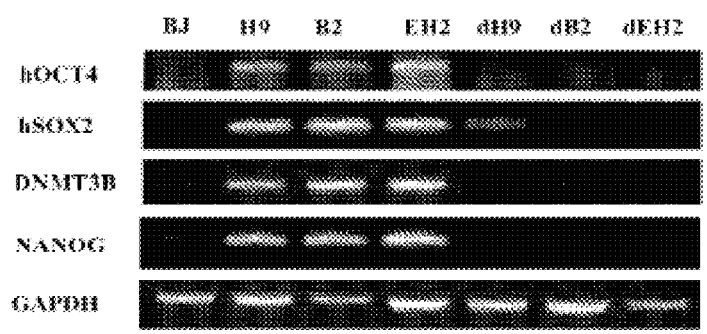

The ReH9 clones expressed SOX2, OCT4, and KLF4 as measured by standard RT-PCR (FIG. 6). Other stem cell markers assayed were: TERT, DNMT3B, NODAL, UTF1, PODXL, and REX1 (Chan et al, 2009). The mRNA for all these markers in the ReH9 iPS lines was expressed at levels typical of hES cell lines (FIG. 6) with the exception of REX1 that was expressed at relatively low levels in the EH2 and EH3 lines. As an additional verification of pluripotency in our cell lines, we subjected some to differentiation in presence of serum and found that the expression of pluripotency markers were extinguished in both our ReH9 iPS cell lines and the hES cell line H9 (FIG. 6b).

Figure 7:
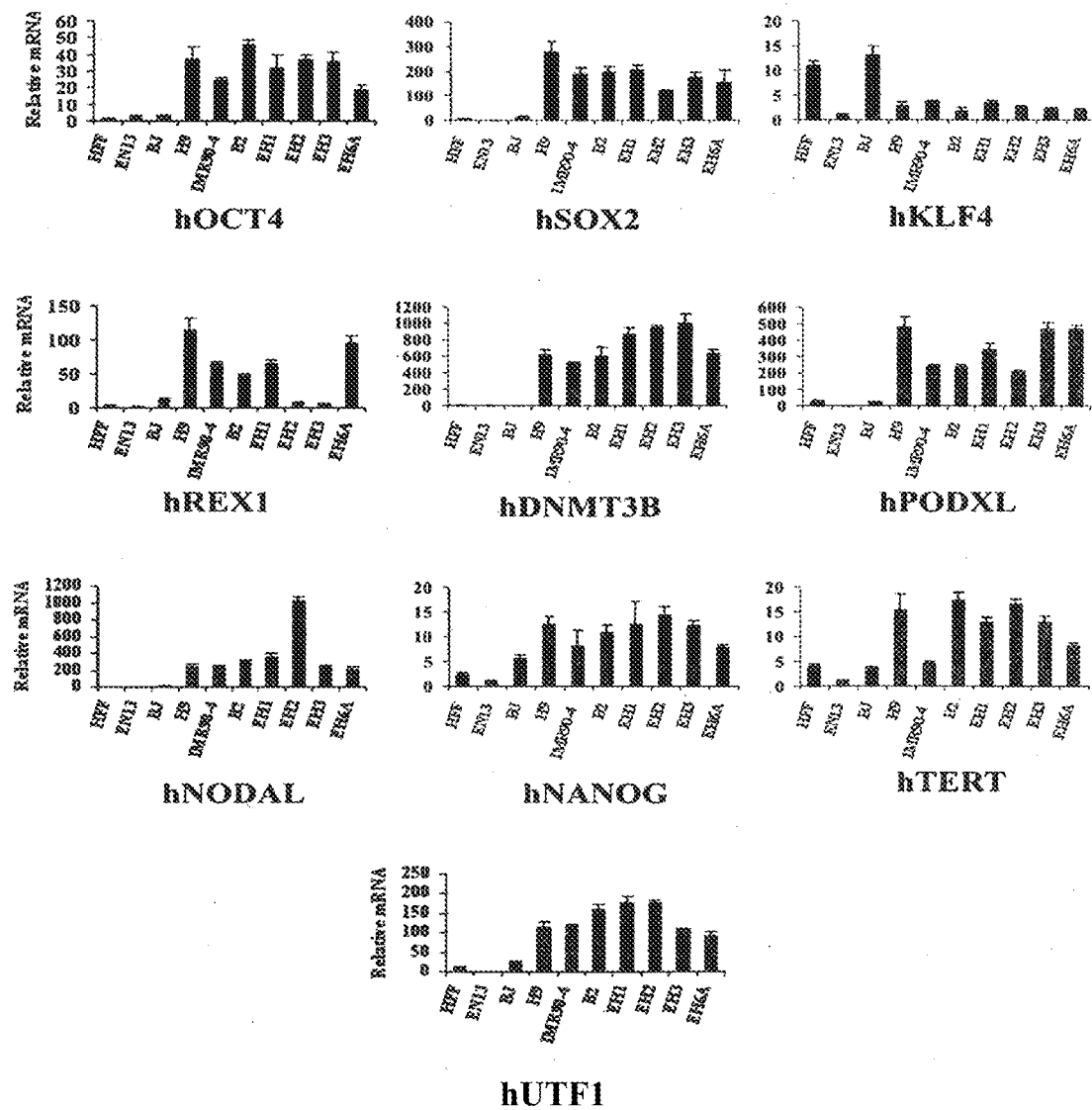
FIG. 7. Expression analysis of pluripotency markers by q-PCR in ReH9 cell lines. The cDNA obtained from RH9 cell lines were subjected to q-PCR analysis in triplicate and the resulting signals normalized to GAPDH controls. Normal controls include normal human foreskin fibroblasts (HFF), the clonal hES-derived embryonic progenitor line EN13, a normal foreskin fibroblast line BJ, the hES cell line H9, and varied iPS cell lines.

In order to verify our results more quantitatively, we also performed quantitative real time PCR (qPCR) for all stem cell markers (FIG. 7). The results confirmed the expression of these markers at levels comparable to hES cells in most of the ReH9 cells, with the exception of EH2 and EH3 that expressed REX1 at low levels. TERT expression levels were relatively higher in iPS and hES cell lines than controls, however no marked differences in expression were observed between the iPS cell lines. Negative controls included three cell lines: HFF, BJ (human diploid fibroblasts) and the target progenitor cell line EN13. All three cell lines showed absence or lower levels of pluripotency factors (FIG. 7). The exception was KLF4, which showed high mRNA levels in HFF and BJ (although the Klf4 protein was low when compared to pluripotent cells (data not shown).

Telomere Length Dynamics in the ReH9 Clones

Figure 8A:
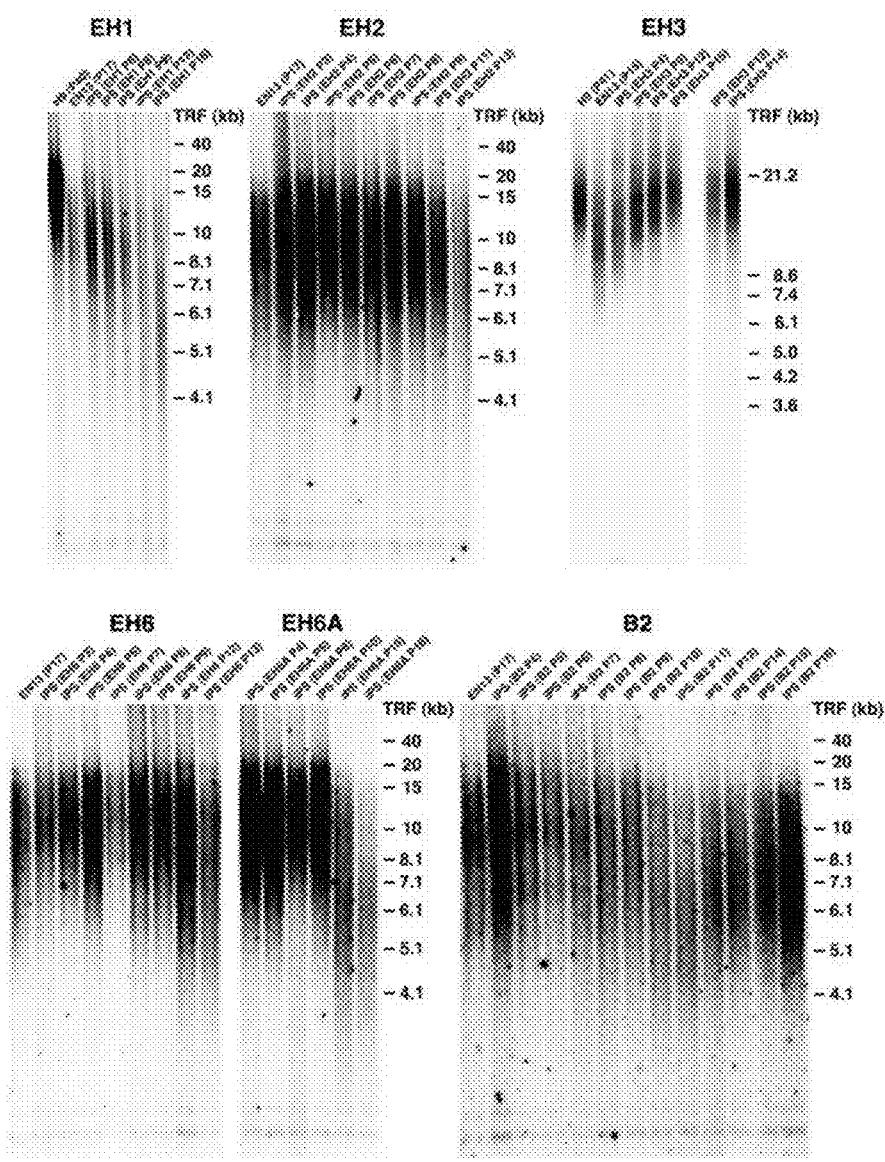
FIG. 8A, FIG. 8B and FIG. 8C. Telomere lengths in EN13-derived iPS cell clones over extended passage.
Figure 8B:
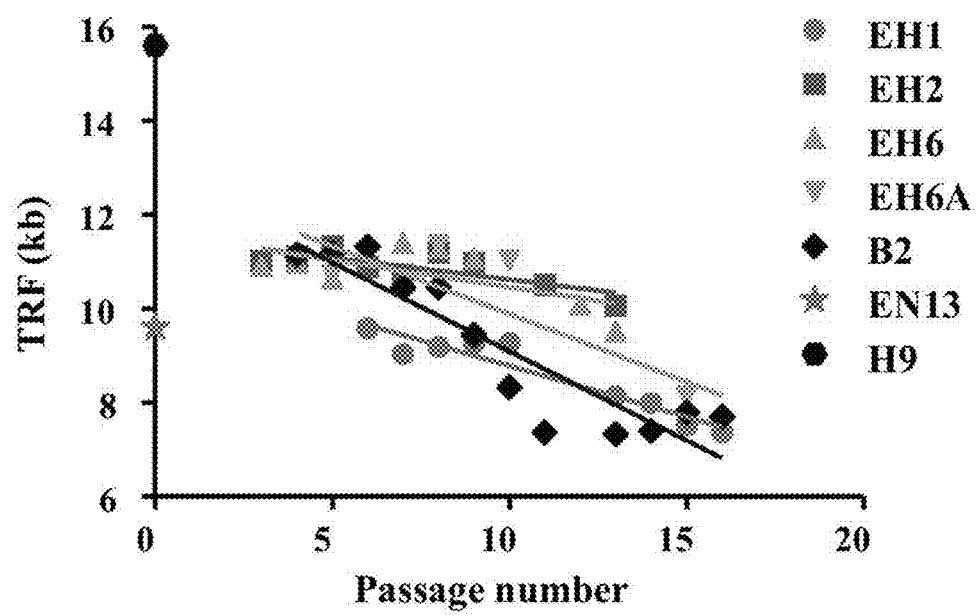
Figure 8C:
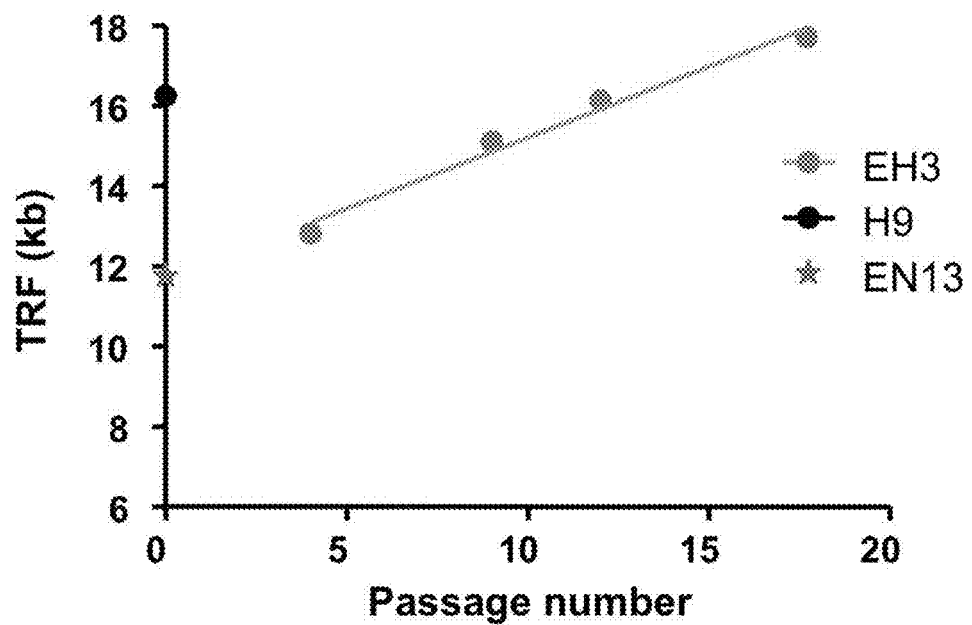

We measured telomere length via Terminal Restriction Fragment (TRF) length analysis as previously described (Vaziri et al, 1993). The six ReH9 cell lines used in this study were subjected to TRF analysis as a function of population doublings. As shown in FIG. 8a,b, shortly after iPS colony isolation, telomere lengths were approximately the length of the starting EN13 cell line mass culture TRF length. In the following passages on Matrigel (i.e. without feeder layers), most clones showed progressive telomere shortening. In the case of EH1, the telomeres were relatively stable until passage 9 (approx 11 PDs post establishment), after which the telomere lengths appeared to destabilize and shorten until P16. Linear regression of the plotted TRF values showed a TRF loss of approximately 22 bp/passage in EH1. A more uniform TRF loss was observed in the lines EH2, EH6, EH6A and B2, with TRF losses of 9 bp/passage, 16 bp/passage, 29 bp/passage, and 38 bp/passage respectively.

In striking contrast to the above, the clone designated EH3 showed progressive telomere elongation from P4 to P13 climbing to approximately 12 kb TRF length with a rate of increase determined by linear regression to be approximately 24 bp/passage (data not shown). In a parallel experiment using cells passaged on murine feeders and transferred to Matrigel for DNA and RNA preparation, the peak TRF length was even more striking (FIG. 8a). At P4 the TRF length measured approximately 12.8 kb, but by P15, the measured TRF climbed to 17.7 kb (FIG. 8a), similar to that of the parental H9 line at P40 with a TRF length averaging 16.25 kb (FIG. 8a) and similar to the mean lengths observed in sperm DNA (Allsopp R C, et al., Proc Natl Acad Sci USA. 1992 Nov. 1; 89(21):10114-8). Linear regression showed a slope of approximately 35 bp/passage. Two EH3 samples were separated from the latter experiment and returned to propagation on Matrigel alone. Those samples were assayed as P13 and P14 and are included in FIG. 8a but not FIG. 8c. Their measured TRF lengths were 15.9 kb and 16.3 kb and when interpreted together with the robust rate of TRF extension of cells grown entirely on Matrigel suggest that the telomere length augmentation observed in EH3 was likely not a result of either culture on or off feeder cells, though the use of feeders gave higher rates of telomere length extension and ultimate TRF length by P15.

Telomerase Activity in ReH9 Cell Lines Compared to H9 hES Cells

Figure 9A:
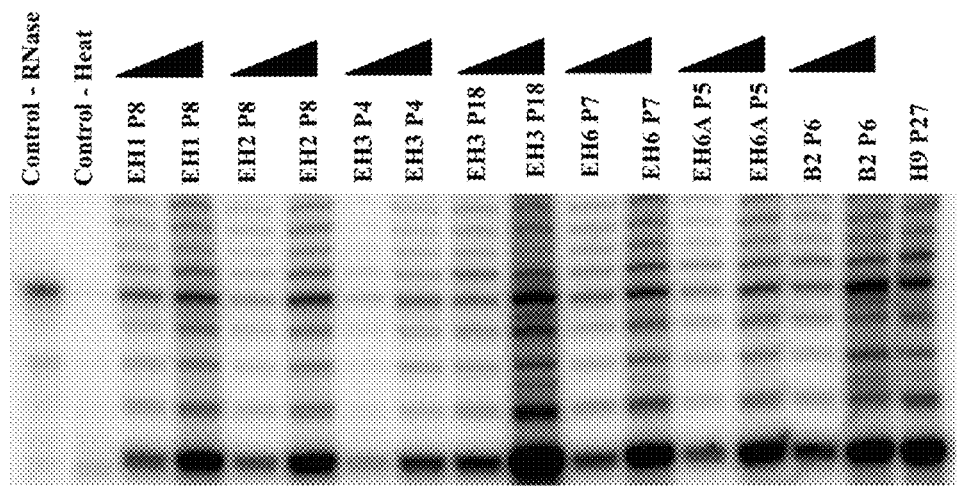
FIG. 9A and FIG. 9B. Telomerase activity levels in RH9 cell lines.
Figure 9B:
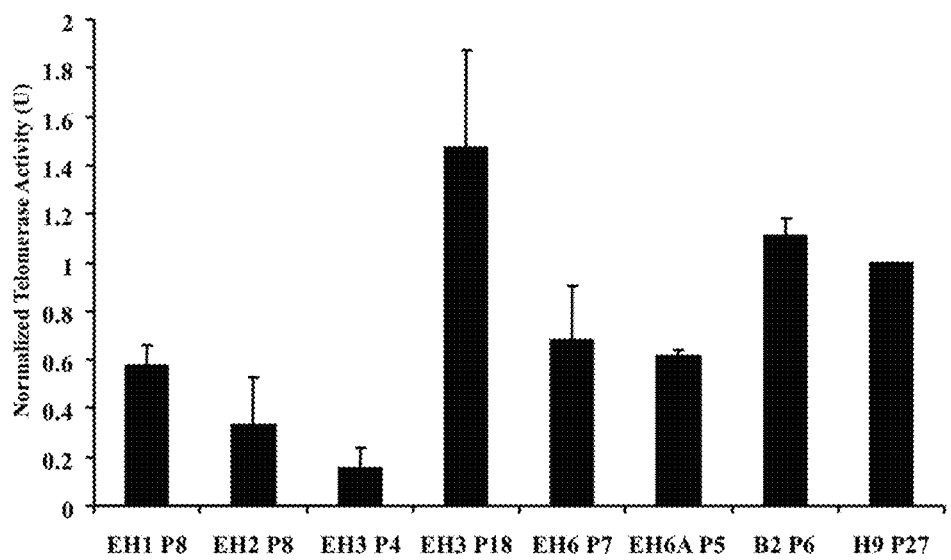

The relative TRAP activity of the ReH9 cell lines normalized by DNA content compared to the parental hES cell line H9 is shown in FIG. 9a and quantified in FIG. 9b. The levels of telomerase activity were generally lower in the ReH9 iPS lines compared to H9, similar to that observed in the surveyed iPS cell lines with the exception of the lines EH3 and B2 both of which showed comparable levels of telomerase activity to H9.

EH3 Karyotype, Pluripotency, and Unique Markers

Figure 10:
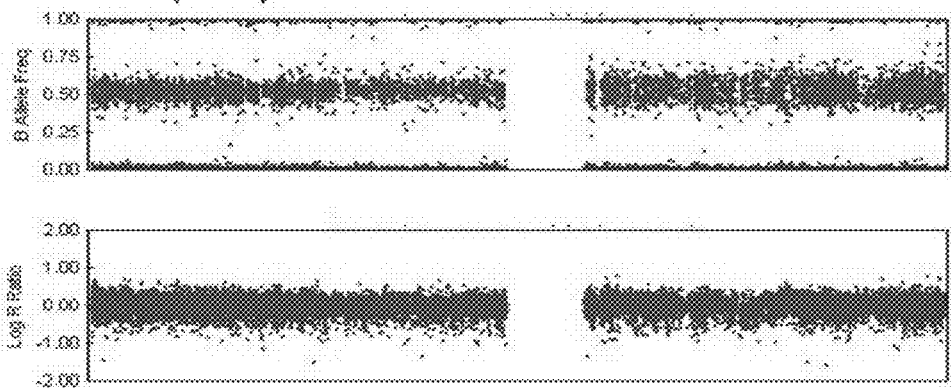
FIG. 10. Chromosome SNP Karyotype.
Figure 10:
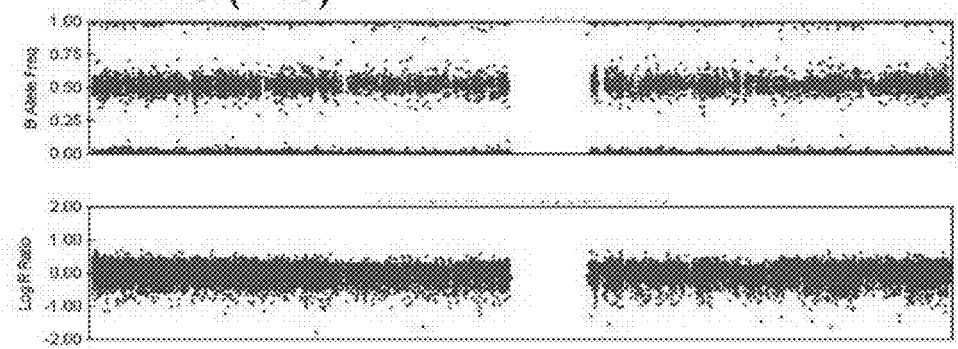
Figure 10:
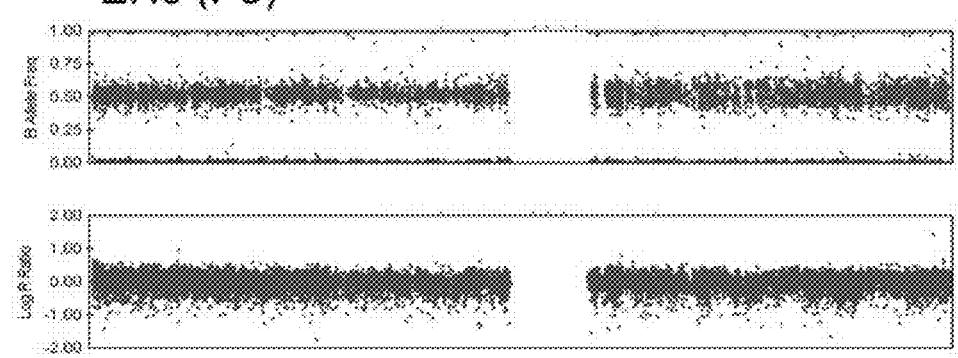

Since the increased telomerase activity and TRF length of EH3 could represent an abnormality of the line, we examined H9, EN13, and EH3 for fine karyotypic abnormalities. We utilized an array-based system, the Illumina CytoSNP12 bead chip, to broadly evaluate over 300,000 SNP markers. A balanced score for both the intensity (log R) and allelic frequency (B allele) are the two most useful indicators of genomic integrity using these systems (Shaikh T H et al, 2009). Each of the cell lines were determined to display a normal karyotype, as assessed by the absence of significant copy number variations (CNVs). A representative assessment of chromosome 1 for the three lines is indicated in FIG. 10 and shows uniform reporting for both log R and B allele frequencies. At the level of resolution of this system (spacing of approximately 10 kb), this assessment provides significantly higher resolution compared to G-banding or other cytological methods, however, a more detailed analysis of potential CNVs would require validation using other methodologies, such as qPCR or FISH. A complete presentation of the log R and B allele frequencies for each chromosome is presented in Supplementary FIG. 3. Therefore, we conclude that a maintenance of a normal karyotype is accurately represented in this isogenic set of cell lines and derivatives and provides a stable basis for interpreting mRNA expression data.

We also tested EH3 (P8) for the ability to form teratomas. The line was cultured for five days (quadruplicate) onto mitomycin C treated MEFs then approximately $5 \times 10^6$ cells of each sample was immediately injected s.c. into the upper flank of anesthetized female NOD-SCID mice (6-8 wks old) for six to eight weeks. All four animals generated palpable tumors.

Figure 11:
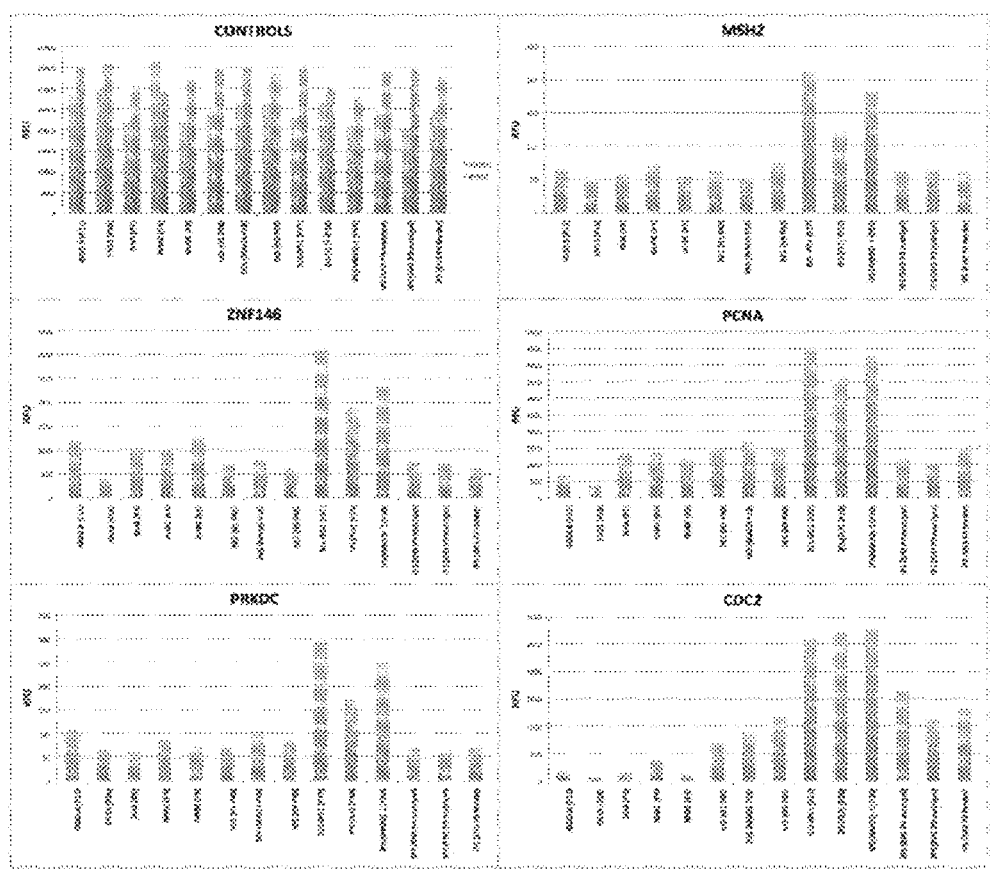
FIG. 11. Telomere-related genes abnormally expressed in established iPS cell lines normally expressed in EH3. Normalized microarray values.

While telomerase activity may provide a useful marker of iPS cell clones capable of telomere length extension to embryonic lengths, additional markers would be useful in the prediction of reprogrammed cells capable of restoring telomeres to normal embryonic TRF lengths. We therefore compared EH3 to the previous lines for the expression levels of the telomere-related genes identified in FIG. 3 as being altered in iPS cells compared to hES cells. The line EH3 was assayed by Illumina microarray and the data was quantile normalized to the data set represented in the heat map of FIG. 3 and the resulting spreadsheet of hybridization values is presented in Supplementary Table I. As shown in FIG. 11, the genes MSH2, ZNF146, PCNA, PRKDC, and CDC2, overexpressed in established iPS cell lines with critically short TRF lengths, appear to be within normal range in the line EH3 when compared to surveyed hES cell lines.

Discussion

The reprogramming of pluripotency and the restoration of embryonic telomere lengths are twin facets of somatic cell reprogramming, each with important implications for the field of regenerative medicine. Assays for the complete reprogramming of differentiation (RD) in a patient's iPS-derived cells is anticipated to provide a means of quality control in the manufacture of clinical-grade cellular therapeutics genetically matched to the patient. The reprogramming of cellular aging (RA) in the absence of developmental reprogramming can be accomplished through the exogenous expression of TERT, however, since the differentiated state of such cells is not affected, such applications are generally limited to cells capable of in vitro expansion such as dermal fibroblasts (Vaziri & Benchimol 1998) or retinal pigment epithelial cells (Bodnar et al 1998) or similar cells capable of expansion in vitro. The observation of reprogramming of development and aging (RDA) in an isogenic background as in this report, provides evidence that RDA may be translated into a manufacturing protocol, opening many new opportunities in basic research and therapeutic development if the reliability of the protocol is optimized.

Further studies are needed to delineate all the limiting parameters for RA in the context of transcriptional reprogramming. All iPS cell lines we surveyed showed markedly short TRF lengths compared to hES cell lines, and iPS (foreskin)-1 (Yu et al, 2007) showed a critical near-senescent TRF length of approximately 6 kb at P52. The foreskin fibroblast line (ATCC number CRL-2097) used for the generation of iPS(foreskin)-1 is reported by ATCC to senesce at approximately 51 doublings from the initial stock culture. Since our assay of TRF length was performed at iPS P52, depending on the rate of growth and the number of doublings in each passage, the TRF length we observed at P52 may reflect the normal rate of senescence of the line without any TRF extension during reprogramming. The rate of telomere attrition observed in our ReH9 lines (other than EH3) ranged from 9-38 bp/passage. Since the number of doublings the iPS cells undergo per passage is not known, it is not possible to compare their rate of loss to normal telomerase (−) cells. But assuming that iPS cells double more than once per passage, it would appear that many iPS cell lines may be losing telomeres, but at a rate slower than telomerase (−) lines.

Also deserving further study is the question of which cocktail of transcription factors or small molecules is most effective at RDA. From the limited data in our survey, BJ1-iPS1 which utilized BJ1-iPS1 OCT4, SOX2, MYC, KLF4, TERT and SV40 large T antigen, where two factors; namely, MYC, a known TERT inducer (Wang J, 1998), and TERT itself, was no more effective at reprogramming TRF length than the combination of LIN28, SOX2, OCT4, and NANOG. Since we observed considerable variability within the clones used in our study all of which utilized the same factors, and TRF lengths varied considerably over in vitro passaging, it seems reasonable to conclude that a comparison of inducing factors as well as culture conditions might help clarify the conditions that optimize RDA.

An example of improvements that might lead to increased reliability of RDA may be the use of cytoplasm of undifferentiated cells such as embryonal carcinoma (EC) cells providing a host of factors similar to the germ-line but enriched in factors such as SOX2, OCT4, NANOG, MYC, LIN28 or TERT (Taranger, C. K. et al, 2005). Since we observed fundamental differences in telosome composition in hES and somatic cells, such as altered expression of TERF1, BLM, and LMNA, as well as other components, the use of germ-line extracts may be useful in improving the restoration of embryonic telomere structure and global gene expression to optimize embryonic progenitors for human therapeutic use (Lillard-Wetherell, K., et al, 2004). Such reprogramming may supply useful factors currently uncharacterized to better mimic the oocyte milieu in SCNT, and has been shown to include the reprogramming of DNA methylation and histone modifications in the regulatory regions of critical genes such as OCT4 and NANOG (Freberg et al, 2007). A comparison of these and other reprogramming protocols will clarify which protocol provides the most reliable modality to reset germ-line telomere length and hES-like gene expression.

The instability we observe in iPS cells derived from embryonic progenitor cell lines, that in turn, were differentiated from hES cells highlights the importance of the use of an isogenic background when studying telomere dynamics. The initial increase in TRF length reported by Suhr S T et al, 2009 may be common in the derivation of iPS cell lines, but later often followed by progressive shortening, perhaps as a result of poor maintenance of the undifferentiated state. This underscores the need for hES cell line controls that themselves are stable and embryonic in length as a measure of whether restoration of embryonic telomere lengths has in fact occurred. Lastly, the results of Feng et al, 2010 showing markedly diminished colony forming ability in hematopoietic and hemangioblastic lineages is consistent with our measurement of critically-shortened TRF lengths in many of the widely-distributed iPS cell lines.

The impact of shortened telomeres on the differentiation of iPS cells remains unknown. While critically-shortened telomeres would be predicted to shorten the replicative lifespan of differentiated progeny cells, cell senescence also profoundly impacts numerous transcriptional pathways that could impact transcriptional cascades associated with differentiation. For example, the Wnt signaling cascade is altered in cell senescence and also plays a critical role in differentiation (Binet R et al, 2009). Further studies are necessary to determine the differentiation potential of iPS cells in the same genetic background with varying telomere lengths using lines such as those in this study.

There are numerous theories of aging in addition to the telomere hypothesis. Some investigators argue that genotoxic events other than telomere shortening or fragmentation, mitochondrial DNA damage, or even somatic mutations (Maynard Smith, 1962) are a more important triggering event in many tissues. However, with the advent of cost-effective whole genome sequencing (Drmanac R et al, 2010), it is now practical to screen somatic cell clones for genomic integrity before reprogramming, thereby generating a desired genotype.

One approach to address these questions regarding the scope of age-reversal in successful RDA is the use of animal models, such as the use of animal iPS cells in the production of germ-line competent chimeras to observe whether normal animals result, similar to studies previously undertaken in the study of SCNT (Lanza R P et al, 2001). SCNT-derived animals provide an effective assay of RDA in that the health profile of the resulting animals can be assessed by existing diagnostic techniques (Cibelli et al, 2002). Initial assays of RA in animals initially suggested that TRF length was abnormally low in SCNT-derived sheep (Shiels et al, 1999). However, subsequent studies demonstrated that RDA was indeed possible, allowing the potential infinite propagation of animal diploid genotypes (Lanza et al, 2000; Kishigami, S. et al, 2008).

Regardless of the scope of age-reversal during reprogramming, the mounting evidence for a role of cellular aging in the pathogenesis of age-related disease (West, 2010) highlights the importance RDA will play in future applications of regenerative medicine in the treatment of age-related degenerative diseases. Age-related degenerative diseases such as age-related macular degeneration (Friedman et al, 2004), osteoarthritis, immune senescence, blood and vascular disorders (Cawthon et al, 2003; American Heart Association, 2006) are often chronic debilitating diseases with disproportionately high cost to society and the quality of life of the individual (Butler, 2008). These and numerous other age-related diseases will be the target of therapeutic strategies in the future using pluripotent stem cell technology (Klimanskaya et al, 2004). The recent report of markedly defective hematopoiesis and early senescence from established iPS cell lines is consistent with the critically-short TRF lengths we report and highlights the importance of TRF length restoration in quality control assays. Even post-mitotic cell types, such as dopaminergic neurons for the treatment of age-related neurodegenerative diseases such Parkinson's disease (Roy et al, 2006), may require sufficient TRF length to allow the commercial scale-up of product.

With the implementation of transcriptional reprogramming protocols in the manufacture of cell-based therapies, interesting questions will arise regarding consequences of the transplantation of embryonic cells and tissues in the aged human, and in the site of age-related pathology. This "heterochronic transplantation" has received little attention to date, with the exception of the heterochronic transplantation of hematopoietic stem cells where (Pipes B L et al, 2006; Schatteman G C & Ma N. 2006). In addition, while not heterochronic in nature, there is a vast history in experimental embryology of the transplantation of embryonic cells and tissues, such as from quail to chick. Early studies in experimental embryology demonstrated a plasticity in tissue transplantation not observed in the fetus or adult. For example, regions of the hindbrain from the quail could be successfully removed and engrafted in the chick, leading to a chimera useful in tracking the fate of populations of cells such as the neural crest (Le Douarin N. Mex., 1984).

RDA will have an important impact on the future management of an aging population. While other strategies to intervene in the biology, such as dietary restriction, show modest effects on slowing the onset of age-related pathology, RDA eventually will have a more expansive impact, allowing the production of young cells of all types for an unlimited period of time. The effective cloning of mammals from old donors without deleterious effects on the offspring suggests that RDA may effectively reverse age-related cellular dysfunction (Jang et al, 1999).

Methods

Generation of ReH9 iPS Clones

The EN13 embryonic progenitor cell line (West et al, 2008) at P11 (PD34) was reprogrammed by infection with pMx-OCT4/pMx-SOX2/pMx-KLF4 viruses (Takahashi et al, 2007). The EN13 cells were first infected with the SOK (SOX2, OCT4 and KLF4) viruses for 20 hours in presence of 8 µg/ml of polybrene. After infection, media was changed and cells were plated on to irradiated feeders (12 Gy). Co-cultures were then switched to knock-out DMEM hES media (Invitrogen, cat#10829-018) containing 16% KOSR media (Invitrogen); 1× Glutamax (Invitrogen); pen/strep (Invitrogen); non-essential amino acids (Invitrogen); 0.6 ml β-Mercaptoethanol (Invitrogen) per 500 ml of media and 50 ng/ml of bFGF (Millipore, cat#GF003). Media was changed daily until iPS colonies appeared. The colonies were manually picked with a pipette tip (p200) or by using plastic cloning rings, washed in PBS and manually removed to 24 well dishes containing radiated feeders. The hES media was changed completely everyday. The cells were subsequently transferred to six well dishes and eventually moved to feeder free 10 cm$^2$ dishes (Corning). Matrigel (BD Bioscience) was thawed at 4° C. and diluted 1:12 with cold DMEM (Invitrogen). A final concentration of 100 ng/ml of bFGF (Millipore) was added to mTSR1 media (Stem Cell Technologies, Vancouver). Media was changed every day and the differentiated or near differentiation colonies were removed. Cell lines were subcultured on average once per week. Colonies were scraped carefully in 2.0 mL of media and spun at 500 rpm for 3 minutes. After removing the supernatant the colonies were gently re-suspended in fresh media and added to Matrigel coated dishes (Greiner, Germany).

TRF Length Measurement

Mean telomere length was measured by the TRF (Telomere Restriction Fragment Length) assay (Vaziri et al, 1993) by radioactive or non-radioactive methods. In brief, hES cells or iPS cells grown on matrigel, lysed in situ by addition of 20 ml of proteinase K buffer and fresh proteinase K (Roche). The lysate was gently collected using soft falcon cell scrapers and digested at 56 deg. C. overnight. The genomic DNA was recovered by standard phenol chloroform extraction and subjected to restriction by HinfI and RsaI. One microgram of restricted DNA was then tested for full digestion and subjected to electrophoresis and Southern blot analysis by using a labeled $^{32}$P-(TTAGGG)$_3$ probe as described. The dried gel was directly exposed to phospho-imager screens and analyzed on a Typhoon phosphoimager (Amersham) and TELORUN software (Vaziri et al, 1993) was utilized to calculate mean TRF length. In the case of non-radioactive assays, EH3 genomic DNA was obtained by column-based extraction with the DNeasy Blood & Tissue Kit (Qiagen). Hybridization utilized the TeloTAGGG Telomere Length Assay kit (Roche, Indianapolis, Ind.) with a digoxigenin-labeled telomere probe. Membranes were probed with an anti-digoxigenin antibody directly conjugated to alkaline phosphatase (AP). TRF signals were visualized by chemiluminescence and detection by Lumi-Film Chemiluminescent Detection Films (Roche) and analyzed as above.

PCR

Total RNA for RT-PCR was purified from cells using Trizol reagent (Invitrogen). First-strand cDNA was synthesized from 100 ng/µl total RNA using a First-Strand cDNA Synthesis Kit (GE Healthcare) according to manufacturer instructions. PCR was carried out on an MJ Research PTC-200 Peltier Thermal Cycler for the genes OCT3/4, SOX2, KLF4, NANOG, TERT, REX1, DNMT3B, PODXL, NODAL, UTFJ, and GAPDH. 50 µl PCR reactions contained 1.0 µl of template cDNA, 1.0 µl each of 10 µM forward and reverse primer, 2.0 µl 10 mM dNTP mix, 5.0 µl of 10× buffer with 1.5 mM MgCl$_2$, and 2.5 units of taq DNA polymerase. Amplified DNA was run on 2% agarose gels in TBE.

Q-PCR was carried out on an MJ Research Opticon 2 system using PerfeCTa SYBR Green SuperMix (Quanta Biosciences, Gaithersburg, Md.). cDNA preparation was the same as for regular RT-PCR. Samples were run in triplicate. H9 was diluted 1:2 for 5 dilutions and run in duplicate as a standards sample for each gene of interest. Efficiencies were calculated from the standard sample dilutions and used to calculate relative initial copy numbers. All signals were then normalized to their respective GAPDH relative initial copy numbers. Samples contained 10 µl of PerfeCTa SYBR Green SuperMix, 0.5 µl each of forward and reverse primers at 10 µM, 4.0 µl of nuclease-free water, and 5.0 µl of template cDNA at 100 ng/µl.

Primers for TERT were forward: 5'-GCGCGTACGA-CACCATCCCC (SEQ ID NO 1), reverse: AAACGCAG-GAGCAGCCCGTC (SEQ ID NO 2), and for NANOG were forward: ACCTTGGCTGCCGTCTCTGG (SEQ ID NO 3), reverse: AGCAAAGCCTCCCAATCCCAAACA (SEQ ID NO 4) designed in Primer3 software (Whitehead Institute). Primers for GAPDH were taken from (Nakamura et al, 1997). All other primer sequences used were taken from (Takahashi, 2007). Staining of pluripotency marker proteins was achieved by first fixing the cells grown on chamber slides in 4% paraformaldehyde followed by three washes in PBS. Primary antibodies against hOct4-P0082 (Sigma)/SSEA4-MC813 (Santa Cruz) were diluted 1:200 and 1:50 respectively. Slides were washed in PBS again and the secondary antibody Alexafluor 488 goat anti-mouse was added at 1:250 and incubated for 15 minutes. Slides were washed and mounted. Fluorescence was detected on a TE-1000 inverted Nikon microscope. Alkaline phosphatase activity was measured by a standard kit per manufacturer protocols (Vector labs).

TRAP Assay:

TRAP assays were performed using a TRAPez Kit (Chemicon). CHAPS lysates were prepared from cells, and aliquots were frozen. Upon thawing, the lysates were subjected to protein quantification using the quick-start Bradford assay system (Biorad). Twenty six cycle PCR-TRAPs were performed in linear range of the assay using 300 ng of total protein lysate per reaction. TRAP products were resolved on 15% polyacrylamide large gels and exposed to phosphorimager screens. HeLa extracts were prepared from HeLa strain ATCC (CCL-2).

Microarray Gene Expression Analysis:

Total RNA was extracted directly from cells growing in 6-well or 6 cm tissue culture plates using Qiagen RNeasy mini kits according to the manufacturer's instructions. RNA concentrations were measured using a Beckman DU530 or Nanodrop spectrophotometer and RNA quality determined by denaturing agarose gel electrophoresis or an Agilent 2100 bioanalyzer. cRNA was hybridized to Illumina whole-genome HumanRef-8 v3.0 BeadArrays, and RNA levels for certain genes were confirmed by quantitative PCR using a Bio-Rad iCycler with an iQ5 multicolor real-time PCR detection system.

Data was read using a BeadStation array reader according to the manufacturer's instructions (Illumina). Data was quantile normalized and otherwise processed using Genespring GX11. Normal cell lines used in the construction of the heat map including normal human astrocytes (NHA), normal human articular chondrocytes (NHA) and human Bronchial epithelial cells (NHBE) were obtained from Lonza.

SNP Karyotyping:

DNA samples for ES line H9, progenitor cell line EN13, and iPS cell line EH3 were assayed using Illumina CtyoSNP12 BeadChip kits (Illumina, San Diego, Calif.) at the Biomedical Genomics Center at the University of Minnesota. The Illumina BeadStudioV2009.2 was used for the detection of copy number variations (CNV) as a sensitive measure of genome integrity and consists of 300K individual SNP markers distributed across the genome. All samples reported with call rates of >99.3%. The data consists of two channel intensities corresponding to the two alleles for each position. The normalized intensity ratios (Log R) and allele frequency (B allele frequency) were calculated and reviewed across each human chromosome for chromosomal aberrations. SNP analysis was carried out using the GenomeStudio Genotyping module (Illumina, Inc., San Diego, Calif.) and DNA copy number changes were visualized using $\log_2$ R ratio and B-allele frequency.

Teratoma Assay:

The iPS cell line EH3 (P8) was seeded (quadruplicate) onto MitC treated MEFs plated on the previous day. Cells were maintained at 37° C., 10% $CO_2$, 5% $O_2$ with daily medium changes. Five days after seeding colonies were collected by using 1 mg/ml collagenase exposure for 15 min followed by scraping and removal with a wide bore pipette. Cells were collected in a sterile conical 50 ml tube, diluted with PBS and spun at 150×g for 5 minutes. Pellets containing approximately $5\times10^6$ cells were gently resuspended in 12 ml of hES medium and shipped cold to Aragen Bioscience, Morgan Hill, Calif. Upon arrival (in 90 minutes) the four tubes were spun at 150 g for 5 min, and the pellets resuspended in 60 ul DMEM/F12 media and transferred to Eppendorf microfuge tubes with the addition of 60 ul of Matrigel. The mixture containing approximately 5×10e6 cells of each sample was immediately injected s.c. into the upper flank of an anesthetized female NOD-SCID mouse (6-8 wks old). Animals were observed daily and noted for formation of teratoma growth. Once, palpable mass was observed, tumor/teratoma growth was measured using a digital caliper twice a week until the teratoma was harvested. After six to eight weeks, the animals were euthanized, the teratomas were excised, bisected sagitally, and then fixed with 4% paraformaldyhyde for 48 hours, and placed in 70% ethanol. Paraffin embedded samples were sectioned at 4 um, and stained with hematoxylin and eosin.

REFERENCES

American Heart Association (2008) Heart disease and stroke statistics-2006 update A report from the American Heart Association Statistics Committee and Stroke Statistics Subcommittee. *Circulation* 113: e85-e151.

Amit M, Carpenter M K, Inokuma M S, Chiu C P, Harris C P, Waknitz M A, Itskovitz-Eldor J, Thomson J A. 2000. Clonally derived human embryonic stem cell lines maintain pluripotency and proliferative potential for prolonged periods of culture. *Dev Biol.* 227(2):271-8.

Binet R, Ythier D, Robles A I, Collado M, Larrieu D, Fonti C, Brambilla E, Brambilla C, Serrano M, Harris C C, Pedeux R. 2009. WNT16B is a new marker of cellular senescence that regulates p53 activity and the phosphoinositide 3-kinase/AKT pathway. *Cancer Res* 69(24): 9183-91.

Bodnar A G, Ouellette M, Frolkis M, Holt S E, Chiu C-P, Morin G B, Harley C B, Shay J W, Lichtsteiner S, Wright W E, (1998) Extension of cell life-span by introduction of telomerase into normal human cells. *Science* 279: 349-352.

Butler, R N (2008) The longevity revolution: the benefits and challenges of living a long life. Public Affairs, New York.

Cawthon R M, Smith K R, O'Brien E, Sivatchenko A, Kerber R A (2003) Association between telomere length in blood and mortality in people aged 60 years or older. *Lancet* 361: 393-395.

Chan, E. M. et al. Live cell imaging distinguishes bona fide human iPS cells from partially reprogrammed cells. *Nat Biotechnol* 27, 1033-1037 (2009).

Chiu, C. P. et al. Differential expression of telomerase activity in hematopoietic progenitors from adult human bone marrow. *Stem Cells* 14, 239-248. (1996).

Cibelli J B, Kiessling A A, Cunniff K, Richards C, Lanza R P, West M D (2001) Somatic cell nuclear transfer in humans: Pronuclear and early embryonic development. e-biomed: *J Regen Med* 2: 25-31.

Cibelli, J. B., Campbell, K. H., Seidel, G. E., West, M. D., Lanza, R. P. 2002. The health profile of cloned animals. *Nature Biotech.* 20: 13-14.

Clark A J, Ferrier P, Aslam S, Burl S, Denning C, Wylie D, Ross A, de Sousa P, Wilmut I, Cui W (2003) Proliferative lifespan is conserved after nuclear transfer. Nat Cell Biol 5(6):535-538

Cooke H J and Smith B A (1986) Variability at the telomeres of the human X/Y pseudoautosomal region. *Cold Spring Harb Symp Quant Biol,* 51 Pt1:213-219

Drmanac R, Sparks A B, Callow M J, Halpern A L, Burns N L, Kermani B G, Carnevali P, Nazarenko I, Nilsen G B, Yeung G, Dahl F, Fernandez A, Staker B, Pant K P, Baccash J, Borcherding A P, Brownley A, Cedeno R, Chen L, Chernikoff D, Cheung A, Chirita R, Curson B, Ebert J C, Hacker C R, Hartlage R, Hauser B, Huang S, Jiang Y, Karpinchyk V, Koenig M, Kong C, Landers T, Le C, Liu J, McBride C E, Morenzoni M, Morey R E, Mutch K, Perazich H, Perry K, Peters B A, Peterson J, Pethiyagoda C L, Pothuraju K, Richter C, Rosenbaum A M, Roy S, Shafto J, Sharanhovich U, Shannon K W, Sheppy C G, Sun M, Thakuria J V, Tran A, Vu D, Zaranek A W, Wu X, Drmanac S, Oliphant A R, Banyai W C, Martin B, Ballinger D G, Church G M, Reid C A. 2010. Human genome sequencing using unchained base reads on self-assembling DNA nanoarrays. *Science.* 327(5961):78-81.

Feng, J., Funk, W. D., Wang, S-S, Weinrich, S. L., Avilion, A. A., Chiu, C-P., Adams, R., Chang, E., Allsopp, R. C., Siyuan Le, J-Y., West, M. D., Harley, C. B., Andrews, W. H., Greider, C. W., Villeponteau, B. V. 1995. The RNA Component of Human Telomerase. *Science.* 269: 1236-1241.

Feng, Q., Lu, S-J., Klimanskaya, I., Gomes, I., Kim, D., Chung, Y., Honig, G. R., Kim, K-S., and Lanza, R. 2010. Hemangioblastic derivatives from human induced pluripotent stem cells exhibit limited expansion an early senescence. Stem Cells 28(4):704-12; Online Feb. 11, 2010.

Freberg C T, Dahl J A, Timoskainen S, Collas, P (2007) Epigenetic reprogramming of OCT4 and NANOG regulatory regions by embryonal carcinoma cell extract. Mol Biol Cell 18:1543-1553.

Friedman D S, O'Colmain B J, Munoz B, Tomany S C, McCarty C, de Jong P T, Nemesure B, Mitchell P, Kempen J (2004) Prevalence of age-related macular degeneration in the United States. Arch Ophthalmol 122: 564-572

Gonzalo S, Jaco I, Fraga M F, Chen T, Li E, Esteller M, Blasco M A. 2006. DNA methyltransferases control telomere length and telomere recombination in mammalian cells. Nat Cell Biol. 8(4):416-24. Epub 2006 Mar. 26.

Halliday T R; Adler K (eds) (1986) Reptiles & Amphibians Torstar Books p 101

Harley, C B, Futcher, A B, Greider, C W (1990) Telomeres shorten during aging of human fibroblasts. *Nature* 345: 458-460

Hayflick L (1965) The limited in vitro lifetime of human diploid cell strains. *Exp Cell Res* 37:614-636

Hayflick L (1992) Aging, longevity, and immortality in vitro. *Exp Gerontol* 27:363-368

Hayflick L, and Moorhead P S (1961) The serial cultivation of human diploid cell strains. *Exp Cell Res* 25:585-621

Huang, Q., Chen, M., et al., 2007. Improving cell therapy—experiments using transplanted telomerase-immortalized cells in immunodeficient mice. Mech. Ageing Dev. 128 (1), 25-30.

Jang G, Hong S G, Oh H J, Kim M K, Park J E, Kim H J, Kim D Y, Lee B C. 2008. A cloned toy poodle produced from somatic cells derived from an aged female dog. Theriogenology. 69(5):556-63.

Kim, N. W., Piatyszek, M. A., Prowse, K. R., Harley, C. B., West, M. D., Ho, P. L. C., Coviello, G. M., Wright, W. E., Weinrich, S. L., and Shay, J. W. 1994. Specific association of human telomerase activity with immortal cells and cancer. *Science,* 266: 2011-2014.

Kishigami, S., Wakayama, S., Hosoi, Y., Iritani, A., and Wakayama, T. 2008. Somatic cell nuclear transfer: Infinite reproduction of a unique diploid genome. *Exp. Cell Res.* 314: 1945-1950.

Klimanskaya I, Hipp J, Rezai K A, West M, Atala A, Lanza R (2004) Derivation and comparative assessment of retinal pigment epithelium from human embryonic stem cells using transcriptomics. Cloning and Stem Cells 6(3):217-245

Kollman C, Howe C W S, Anasetti C, Antin J H, Davies S M, Filipovich A H, Hegland, J, Kamani, N, Kernan, N A, King, R, Janet Hegland, Naynesh Kamani, Nancy A. Kernan, Roberta King, Ratanatharathorn V, Weisdorf D, and Confer D L. 2001. Donor characteristics as risk factors in recipients after transplantation of bone marrow from unrelated donors: the effect of donor age. *Blood* 98: 2043-2051.

Lanza, R. P., Cibelli, J. B., and West, M. D. 1999a. Prospects for the use of nuclear transfer in human transplantation. *Nature Biotechnology* 17(12): 1171-1174.

Lanza, R. P., Cibelli, J. B., and West, M. D. 1999b. Human therapeutic cloning. *Nature Medicine* 5(9): 975-977.

Lanza, R. P., Cibelli, J. B., Blackwell, C., Cristofalo, V. J., Francis, M. K., Baerlocher, G. M., Mak, J., Schertzer, M., Chavez, E. E., Sawyer, N, Lansdorp, P. M., and West, M. D. 2000. Extension of cell life-span and telomere length in animals cloned from senescent somatic cells. *Science* 288: 665-669.

Lanza, R. P., Cibelli, J. B., Faber, D., Sweeney, R. W., Henderson, B., Nevala, W., West, M. D., and Wettstein, P. J. 2001. Cloned animals can be healthy and normal. *Science* 294(5548): 1893-1894.

Lanza R, Moore M A, Wakayama T, Perry A C, Shieh J-H, Hendrikx J, Leri A, Chimenti S, Monsen A, Nurzynska D, West M D, Kajstura J, Anversa P (2004) Regeneration of infarcted heart with stem cells derived by nuclear transplantation. Circ Res 94(6):820-827

Le Douarin N M. (1984) Ontogeny of the peripheral nervous system from the neural crest and the placodes: A developmental model studied on the basis of the quail-chick chimaera system. Harvey Lect. 1984-1985; 80:137-186.

Lee H W, Blasco M A, Gottlieb G J, Homer J W $2^{nd}$, Greider C W, DePinho R A (1998) Essential role of mouse telomerase in highly proliferative organs. Nature 392: 569-574.

Li, X., Sun, L., and Jin Y. 2008. Identification of karyopherin-alpha 2 as an Oct4 associated protein. J. Genet. Genomics. 35(12):723-728.

Lillard-Wetherell K, Machwe A, Langland G T, Combs K A, Behbehani G K, Schonberg S A, German J, Turchi J J, Orren D K, Groden J (2004) Association and regulation of the BLM helicase by the telomeric proteins TRF1 and TRF2. Hum Mol Genet 13:1919-1932.

Lund R D, Wang S, Klimanskaya I, Holmes T, Ramos-Kelsey R, Lu B, Girman S, Bischoff N, Sauvé Y, Lanza R. 2006. Human embryonic stem cell-derived cells rescue visual function in dystrophic RCS rats. Cloning Stem Cells 8(3):189-99.

Mantell, L. L. & Greider, C. W. Telomerase activity in germline and embryonic cells of Xenopus. *Embo J* 13, 3211-3217 (1994).

Marion R M, Strati K, Li H, Tejera A, Schoeftner S, Ortega S, Serrano M, Blasco M A. 2009. Telomeres acquire embryonic stem cell characteristics in induced pluripotent stem cells. *Cell Stem Cell* 4(2):141-54.

Maynard Smith, J. 1962. Review Lectures on Senescence: I. The causes of aging. *Proc. R. Soc. Lond. B* 1962 157, 115-127.

McLaren A (1992) Embryology The quest for immortality. *Nature* 359:482-483

McLaren A (2001) Mammalian germ cells: birth, sex, and immortality. *Cell Struct Funct* 26:119-122.

Nakamura T M, Morin G B, Chapman K B, Weinrich S L, Andrews W H, Lingner J, Harley C B, Cech T R (1997) Telomerase catalytic subunit homologs from fission yeast and human *Science* 277:955-959

Olovnikov A M (1971) Principles of marginotomy in template synthesis of polynucleotides. *Doklady Akad Nauk SSSR* 201:1496-1499.

Park I H, Zhao R, West J A, Yabuuchi A, Huo H, Ince T A, Lerou P H, Lensch M W, Daley G Q. 2008. Reprogramming of human somatic cells to pluripotency with defined factors. Nature. 451(7175):141-6. Epub 2007 Dec. 23.

Pipes B L, Tsang T, Peng S X, Fiederlein R, Graham M, Harris D T. 2006. Telomere length changes after umbilical cord blood transplant. Transfusion 46(6):1038-43.

Riethman, H. Ambrosini, A., and Paul, S. 2005. Human subtelomere structure and variation. Chrom. Res. 13(5): 505-515.

Rosier, E S., Fisk, G. J., Ares, X., Irving, J., Miura, T., Rao, M. S., and Carpenter, M. K. 2004. Long-term culture of human embryonic stem cells in feeder-free conditions. *Dev. Dyn.* 229:259-274.

Roy N S, Cleren C, Singh S K, Yang L, Beal M F, Goldman S A (2006) Functional emgraftment of human E S cell-derived dopaminergic neurons enriched by coculture with telomerase-immortalized midbrain astrocytes. *Nat Med* 12:1259-1268.

Rufer N, Brummendorf T H, Kolvraa S, Bischoff C, Christensen K, Wadsworth L, Schulzer M, Lansdorp P M (1999) Telomere fluorescence measurements in granulocytes and T lymphocyte subsets point to a high turnover of hematopoietic stem cells and memory T cells in early childhood. *J Exp Med* 190:157-167.

Schaetzlein, S. et al. Telomere length is reset during early mammalian embryogenesis. *Proc Natl Acad Sci USA.* 101, 8034-8038. Epub 2004 May 8017. (2004).

Schatteman G C, Ma N. 2006. Old bone marrow cells inhibit skin wound vascularization. *Stem Cells* 24(3):717-21. Epub 2005 Nov. 3.

Shaikh T H, Gai X, Perin J C, Glessner J T, Xie H, Murphy K, O'Hara R, Casalunovo T, Conlin L K, D'Arcy M, Frackelton E C, Geiger E A, Haldeman-Englert C, Imielinski M, Kim C E, Medne L, Annaiah K, Bradfield J P, Dabaghyan E, Eckert A, Onyiah C C, Ostapenko S, Otieno F G, Santa E, Shaner J L, Skraban R, Smith R M, Elia J, Goldmuntz E, Spinner N B, Zackai E H, Chiavacci R M, Grundmeier R, Rappaport E F, Grant S F, White P S, Hakonarson H. 2009. High-resolution mapping and analysis of copy number variations in the human genome: a data resource for clinical and research applications. *Genome Res.* 19(9):1682-90. Epub 2009 Jul. 10.

Shamblott, M. J. et al. Derivation of pluripotent stem cells from cultured human primordial germ cells. *Proc Natl Acad Sci USA* 95, 13726-13731 (1998).

Shawi, M. and Autexier, C. 2008. Telomerase, senescence, and aging. *Mech. Aging Dev.* 129: 3-10.

Shay, J. W. and Wright, W. E. 2005. Use of telomerase to create bioengineered tissues. *Ann NY Acad Sci* 1057: 479-491.

Shiels P G, Kind A J, Campbell K H, Waddington D, Wilmut I, Colman A, Schnieke A E (1999) Analysis of telomere lengths in cloned sheep. *Nature* 399(6734):316-317

Slagboom P E, Droog S, Boomsma D I (1994) Genetic determination of telomere size in humans: A twin study of three age groups. *Am J Hum Genet* 55:876-882

Suhr S T, Chang E A, Rodriguez R M, Wang K, Ross P J, Beyhan Z, Murthy S, Cibelli J B. 2009. Telomere dynamics in human cells reprogrammed to pluripotency. *PLoS One* 4(12):e8124.

Takahashi K, Tanabe K, Ohnuki M, Narita M, Ichisaka T, Tomoda K, Yamanaka S. 2007. Induction of pluripotent stem cells from adult human fibroblasts by defined factors. *Cell* 131: 861-72.

Taranger C K, Noer A, Sorensen A L, Hakelien A M, Boquest A C, Collas P (2005) Induction of dedifferentiation, genomewide transcriptional programming, and epigenetic reprogramming by extracts of carcinoma and embryonic stem cells. *Mol Biol Cell* 16:5719-5735.

Thomson J A, Itskovitx-Eldor J, Shapiro S S, Waknitz M A, Swiergierl J J, Marshall V S, Jones, J M (1998) Embryonic stem cell lines derived from human blastocysts. *Science* 282:1145-1147.

Vaziri, H. et al. Loss of telomeric DNA during aging of normal and trisomy 21 human lymphocytes. *Am J Hum Genet* 52, 661-667. (1993).

Vaziri, H., Benchimol, S., 1998. Reconstitution of telomerase activity in normal human cells leads to elongation of telomeres and extended replicative life span. *Curr. Biol.* 8, 279-282.

Wakayama T, Shinkai Y, Tamashiro K L, Niida H, Blanshard D C, Ogura A, Tanemura K, Tachibana M, Perry A C, Colgan D F, Mombaerts P, Yanagimachi R (2000) Cloning of mice to six generations. *Nature* 407(6802):318-319

Wang J, Xie L Y, Allan S, Beach D, Hannon G J. 1998. Myc activates telomerase. *Genes Dev.* 12(12):1769-74.

Weismann A 1891. Essays upon heredity and kindred biological problems Vol I, Clarendon Press.

West, M. D. 2010. Embryonic stem cells: Prospects of regenerative medicine for the treatment of human aging. In *The Future of Aging.* (Eds Fahy, G. M., West, M. D., Coles, L. S., and Harris, S. B.) Springer (In Press).

Widmann T, Kneer H, Konig J, Herrmann M, Pfreundschuh M. 2008. Sustained telomere erosion due to increased stem cell turnover during triple autologous hematopoietic stem cell transplantaion. *Exp Hematol.* 36(1):104-10. Epub 2007 Oct. 18.

Wilmut I, Schnieke A E, McWhir J, Kind A J, Campbell K H (1997) Viable offspring derived from fetal and adult mammalian cells. *Nature* 385(6619):810-813

Wright, W. E., Piatyszek, M. A., Rainey, W. E., Byrd, W. & Shay, J. W. Telomerase activity in human germline and embryonic tissues and cells. *Dev Genet.* 18, 173-179. (1996).

Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A (2007) Induced pluripotent stem cell lines derived from human somatic cells. *Science* 318:1917-1920.

Example 2

Gene expression analysis was performed on a series of different cell populations/cell lines and the level of VENTX expression was compared (gene expression analysis methods described in Example 1).

Figure 14A:
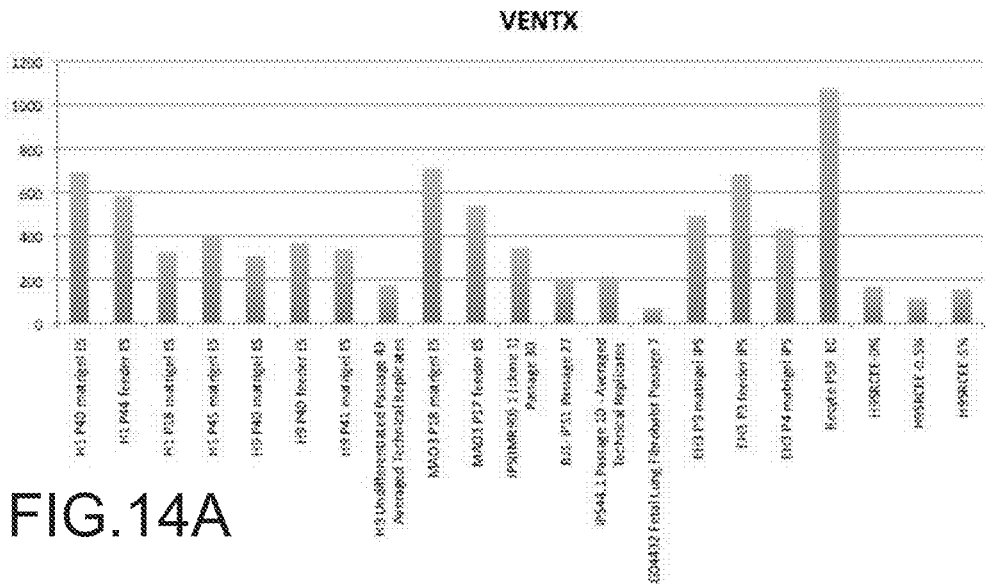
FIG. 14A and FIG. 14B. VENTX expression is increased in cells that can restore telomere to embryonic lengths.
Figure 14B:
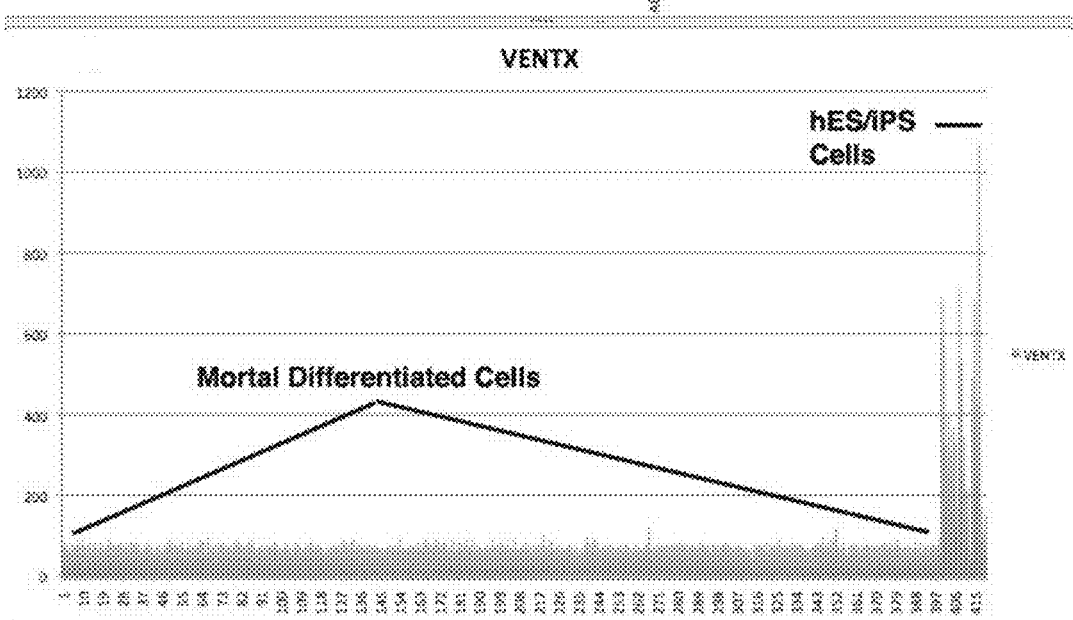

Panel A of FIG. 14 shows relative VENTX expression levels for numerous different human ES (H1, H9, MAG3) and iPS (IMR90-1, BJ1, 44.1, EH3) cell lines that can reset telomeres to embryonic lengths (at specific passages/culture conditions as indicated) as well as the embryonic carcinoma (EC) cell line Recyte P59 and the fetal lung fibroblast line AG04432 at passage 7. As can be seen in Panle A, VENTX expression is relatively high in cell lines having telomere lengths restored to embryonic levels.

Panel B of FIG. 14 shows that VENTX expression in numerous differentiated mortal cells of many different cell types is at or near background levels, whereas VENTX expression in a variety or human ES and iPS cell lines having telomere lengths restored to embryonic levels is well above background. Thus, VENTX expression level can be used as a marker for high quality ES and iPS cell lines, i.e., those having, or capable of generating, telomeres with lengths similar to embryonic cells.

Example 3: Gene Expression Assays Predicting the Potential for Reprogrammed Cells to Spontaneously Immortalize Normal human somatic cells invariably senesce when serially cultivated in vitro (Hayflick L (1965) The limited in vitro lifetime of human diploid cell strains. Exp Cell Res 37:614-636). Exceptions to this rule are undifferentiated human embryonic stem cell lines and iPS cell lines that express telomerase activity (as described herein), abnormal cells that have undergone malignant transformation, or somatic cells in which the catalytic component of telomerase TERT has been exogenously expressed.

Differentiated clonal embryonic progenitors were derived from the parental iPS cell line EH3 at passage 8 (P8), which was derived from the cell line EN13. As described above, EH3 was show to have restored telomere length (see FIG. 8 and its description above). The method used to derive the clonal embryonic progenitor cell lines was described previously (see US Patent Publication No. 2008/0070303 titled "Methods to accelerate the isolation of novel cell strains from pluripotent stem cells and cells obtained thereby"; US Patent Publication No. 2010/0184033 titled "Methods to accelerate the isolation of novel cell strains from pluripotent stem cells and cells obtained thereby"; and West et al, 2008. The ACTCellerate Initiative: large-scale combinatorial cloning of novel human embryonic stem cell derivatives. Regen. Med. 3(3): 287-308; each of which incorporated herein by reference). Of these clonal progenitor cell lines, six named 14-SKEL-7X, 14-SKEL-18X, 14-SKEL-24Z, 14-PEND-23X, 14-PEND-2X, 14-SMOO-2X were serially passaged to determine their replicative lifespans in vitro.

Figure 15:
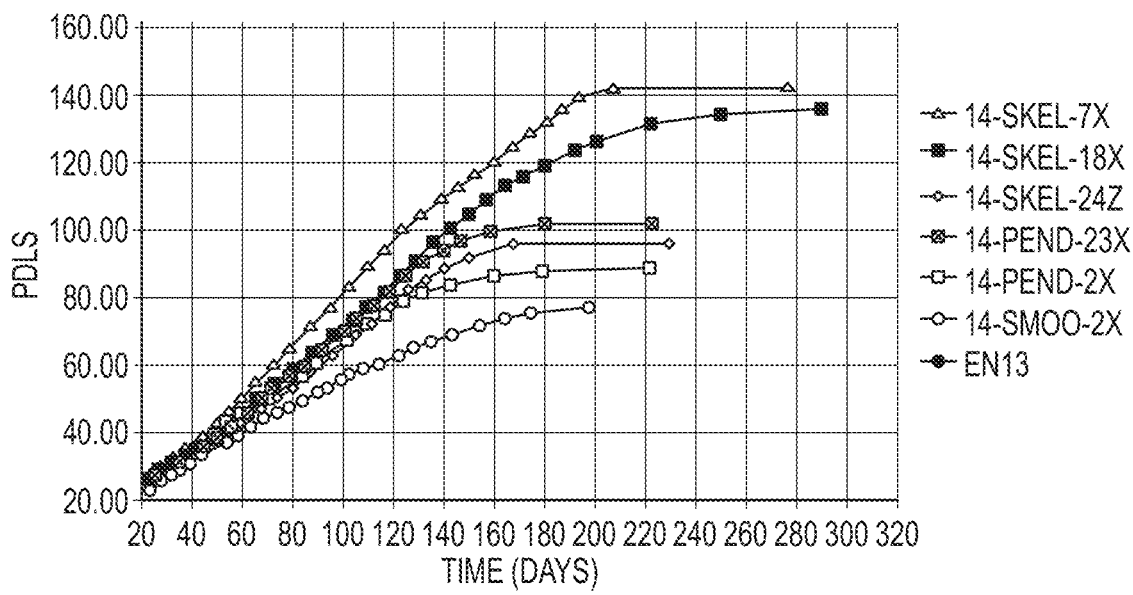
FIG. 15. Cell lifespan analysis. Population Doublings (PDLs) over time (days) for the original line EN13 and clonal embryonic progenitor cell lines derived from EH3 at P8 are shown.

FIG. 15 shows the cell lifespan of the original line EN13, and each of the clonal embryonic progenitor cell lines derived from EH3 at P8 (except 14-SMOO-2X). As shown in FIG. 15, each of the cell clones proliferated far beyond the lifespan of the line EN13, indicating that the increase in telomere length observed in EH3 increases cell lifespan in its mortal somatic cell derivatives. The choice of reprogrammed cells that show the increased telomere length as described in the paper actually leads to an increased cell lifespan.

Figure 16:
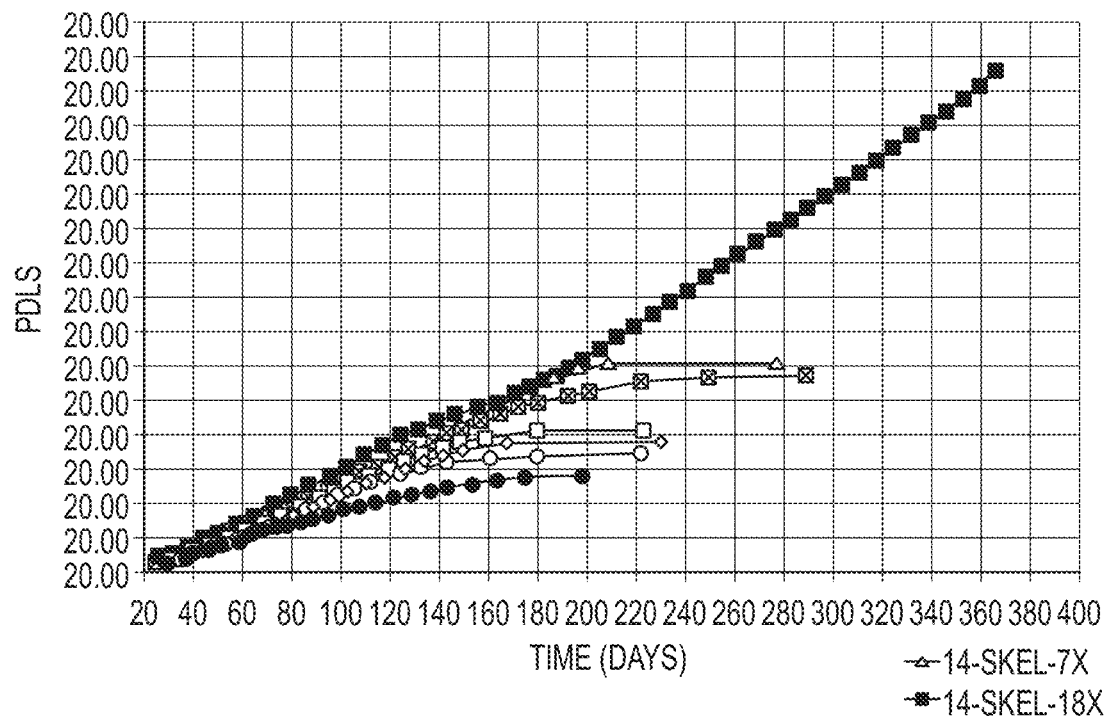
FIG. 16. Immortalization. Population Doublings (PDLs) over time (days) for the original line EN13 and clonal embryonic progenitor cell lines derived from EH3 at P8 are shown. The clonal embryonic progenitor cell line 14-SMOO-2X showed no evidence of senescence after greater than 300 doublings and no evidence of a crisis event.

With the exception of 14-SMOO-2X, the cell lines senesced after a range of approximately 80-140 doublings. However, the clonal embryonic progenitor cell line 14-SMOO-2X showed no evidence of senescence after greater than 300 doublings and no evidence of a crisis event such as is observed in the process of immortalization with viral oncogenes like SV40 virus T-antigen (see FIG. 16). As is well-known in the art, a replicative lifespan of 300 doublings in human somatic cells is clear evidence of an immortal phenotype. The cell line was tested and determined to be abnormally telomerase positive.

An examination of 14-SMOO-2X gene expression by Illumina microarrays as described herein compared to similar diverse clonal embryonic progenitor cell lines produced from the normal hES cell line H9 and MA03, showed that the cell line 14-SMOO-2X abnormally expressed the genes OCT4 (POU5F1) accession number NM_002701.4 and POU5F1P1 accession number NR_002304.1 that is generally only expressed in hES cells but not clonal embryonic progenitors. The cell line 14-SMOO-2X did not, however, express NANOG, SOX2, LIN28, or KLF4. Therefore the expression of OCT4 (POU5F1) accession number NM_002701.4 and POU5F1P1 accession number NR_002304.1 (i.e. the lack of repression) in differentiated cells derived from pluripotent stem cells resulting from the reprogramming of somatic cells is indicative of a risk of abnormal immortalization and a risk of the cell transforming into malignant cells. The expression in somatic cells derived from iPS cells (or similar pluripotent stem cells resulting from the reprogramming of somatic cells) of OCT4 (POU5F1) accession number NM_002701.4 or POU5F1P1 accession number NR_002304.1 can be assayed by microarrays, qPCR, the use of antibodies to detect the protein, and similar assays well-known in the art. If one or both of these genes is not repressed (the expression level is above a threshold level), the cells are categorized as being at risk of transformation or spontaneous immortalization, which can exclude them from certain clinical applications.

Example 4: Genetic Integrity

Many reports have documented genome alterations that occur with prolonged culture of embryonic stem cells and their derivatives and a subset of these defects have been correlated to tumorigenic propensities (Werbowetski-Olgivie et al., 2009). In addition, cellular re-programming technologies, such as induced pluripotent stem cell (iPS) derivations rely on the activities of a variety of proto-oncogenes to achieve pluripotency which can result in genomic abnormalities (Laurent et al., 2011). Cell therapies that rely on transgenic alteration of the genome can include random integration strategies of unknown consequence. Thus, assessing the genomic and genetic integrity of cultured human cells is now a critical part of the manufacturing quality control process.

Currently, the application of low resolution karyotyping based on G-banding is commonly used to assess the chromosomal integrity of cell populations and can clearly be useful in describing the gross alterations of the genome. A combination of modern molecular methodologies can provide a higher resolution of sequence/genetic integrity. Such genetic integrity assessment procedures can be applied to the initial cell population (for example, embryonic stem cell, induced pluripotent stem cell, etc.) and to the final transplant-ready derivative population (for example, derived neuronal cells, pancreatic β-islet cells, etc.) and can be used to monitor the integrity of the cells at any point during the derivation and manufacturing process.

Defining the cell population using "molecular fingerprinting" techniques allows confirmation of the identity of the preparation at any time during the derivation or manufacturing process. A variety of such marker sets are available including variable number tandem repeats (VNTRs) or short tandem repeats (STRs) and can unambiguously define the genotype of a cell preparation (except for monozygotic identical twins). These molecular fingerprints allow for the tracking of cell lines even when altered (i.e., by application of transgenic or iPS technologies) or following differentiation or derivation.

Cytogenetic techniques, such as G-banding of chromosome spreads, is applied to ensure that overall chromosome count and composition is normal. This typically involves the scoring of at least 20-50 or more individual nuclei to arrive at a meaningful assessment. Cytogenetic methods have the advantage of quickly identifying large scale polyploidy and structural aberrations, such as inversions, deletions and translocations.

Culture mosaicism is an important consideration for cell therapeutics manufacturing. Genomic alterations in cell cultures often initiate in a small minority of cells. If these alterations confer a growth advantage to the cell (for example, by reducing the cell generation time), the altered cells can eventually overtake the "normal" cells in the culture. Transplantation of mosaic cultures could have important implications, since it is expected that abnormal cells with enhanced growth potential could endanger the patient. Thus it is important to identify any abnormal cells within a cell preparation, even if they represent a small fraction of the overall population. Fluoresence in situ hybridization (FISH), comparative genomic hybridization (CGH) and other related cytogenetic techniques can be employed for this purpose. As one example, analysis can be accomplished by applying multiple FISH probes covering genes that have been documented to become polyploidy as a result of long-term culture (for example, 12p and 17 centromere probes). Increasing the number of nuclei analyzed by these methods increases the sensitivity of detection; a count of 200 interphase nuclei typically would allow detection sensitivity of less than 5% altered genomes.

More advanced, high resolution molecular techniques for karyotypic assessment include the use of high density probe arrays to detect copy number variations (CNVs). These methods typically employ the detection of SNPs within the genome or CGH arrays to assess the copy number of specific loci. Depending on the density of molecular probes used, the resolution of these methods can typically identify CNVs of size 10 kbp or larger. Identification of regions with copy number variation then allows for the informatics assessment of affected genes within these regions. For example, identification of a region that is hemizygous (n=1) would be of greater concern in the analysis of genomic integrity if this same region contained a gene, or genes, that have been described as tumor suppressors. Similarly, regions that are polyploidy (n>2) would be of concern if they contained genes that have been described as growth factors or oncogenes.

Fully analyzing and documenting the complete DNA sequence of cellular therapeutics is the highest resolution of genetic analysis. To date, the number of documented genetic disease with clearly defined gene/phenotype relations is over 300, while the number with Mendelian phenotype and an as yet undefined molecular lesion is over 1600 (Online Mendelian Inheritance in Man). Since the vast majority of these disorders do not affect early embryonic development, it would be unlikely that these would result in clearly defined phenotypes in embryonic stem cell cultures. Furthermore, since embryonic stem cell lines by derivation have not progressed through an adult phase, it can be important to ensure that cell therapeutics derived from ES lines are assessed for genetic disease.

Currently, complete genome sequencing can be accomplished by many methods, including oligonucleotide-based hybridization methods (Complete Genomics, Mtn. View, Calif.), bead-based dye-terminator methods (Illumina; San Diego, Calif.); and many others (Metzker, 2009). Typically, these methods analyze the human genome by comparison to a reference genome (or genome build) and then compile a list of all variant seen in the sample genome being tested. Current informatics applications for whole genome sequencing can provide a single nucleotide resolution for the genome. The assessment of variation within the genome of a cell preparation can include the following detail:

1. Integrity of coding sequences for all known and predicted human genes and transcripts. Identifying variants that include nonsense, disruptive missense, frameshifting insertions or deletions, splice donor/acceptor defects can then be used to define mutation sets that should be further reviewed. For example, a disruptive mutation in a tumor suppressor gene would be of significance since this could represent a genotype with increased propensity for abnormal growth or even oncogenic transformation.

2. Review of deleterious mutations in the coding sequences of genes required for biological function. Cell-based therapeutics are often deployed in regenerative medicine where they are expected to restore normal tissue function. For example, if the therapeutic is applied to restore normal cartilage function, a thorough review of all genes who's activities are required for normal cartilage production and maintenance is an important assessment.

3. Review of Disease propensity alleles. Large compendiums of human variants associated with human disease are available and represent an important consideration for human therapeutics. (www(dot)genome(dot)gov/gwastudies/). For example, the ApoE4 allele is associated with substantial risk for developing neurodegenerative disease, such as Alzheimer's dementia, and for increased risk for developing cardiovascular disease. Conversely, the ApoE2/3 alleles do not confer this risk. When assessing cell lines for therapeutic development, it would be advantageous to analyze and avoid cell preparations that encode non-advantageous alleles.

4. Review of common genetic disease phenotypes. Large databases that compile defined human mutations are available (for example www(dot)hgmd(dot)cf.ac.uk/ac/index(dot)php). Comparison of identified variants in the test genome to such collections can define mutations that could be of consequence for therapeutic application. For example, ensuring that the cell therapeutic destined for application in muscular dystrophy does not encode know mutations within the DMD gene would be necessary.

5. Review of transplant-related antigens. HLA (and MHC) alleles can be directly assessed by a review of complete genome sequencing. Avoiding known high risk propensity alleles for HLA (i.e., HLA-DQ alleles corresponding to autoimmune disease, Crohn's Disease etc.) would be recommended. Similarly, selecting O/O negative cell lines for the production of blood cell products, or selecting female cell lines for typical cell therapy development may be of advantage.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

length analysis (STELA), fluorescence in-situ hybridization (FISH), flow-FISH, and Southern blot analysis.

3. The method of claim 1, further comprising: evaluating the expression level of at least one additional gene in the induced pluripotent stem cell line to obtain a gene expression level result, wherein the at least one additional gene is selected from one or more of: PCNA, CDC2, MSH2, ZNF146, TERF1 transcript variant 2, VENTX and PRKDC; and selecting the induced pluripotent stem cell line as a pluripotent stem cell line suitable for clinical use based on thecomparing the gene expression level results to a reference gene expression level result, wherein the reference gene is selected from one or more of: PCNA, CDC2, MSH2, ZNF 146, TERF1 transcript variant 2 and PRKDC.

4. The method of claim 3, wherein the reference gene expression level result is from embryonic stem cells and wherein the expression of the at least one gene in the induced pluripotent stem cell line is equivalent to the reference gene expression level result.

5. The method of claim 1, further comprising:
v) assessing the genomic integrity of the induced pluripotent stem cell line to obtain a genomic integrity result, wherein said assessing comprises one or more of: karyotyping; analysis of variable number tandem repeats (VNTRs), short tandem repeats (STRs), single nucleotide polymorphisms (SNP), and/or copy number variations (CNVs); analysis of culture mosaicism; analysis of DNA sequences related to genetic diseases; and complete genome sequencing and analysis; and

What is claimed is:

1. A method of selecting an induced pluripotent stem cell line suitable for clinical use, the method comprising:
   i) obtaining an induced pluripotent stem cell line, wherein the cells of the induced pluripotent stem cell line comprises exogenous SOX2, OCT4 and KLF4;
   ii) evaluating telomere length of the induced pluripotent stem cell line from i); and
   iii) selecting the induced pluripotent stem cell line if the evaluated telomere length comprises a mean telomere restriction fragment length of about 12 kb or more
   iv) evaluating VENTX expression in the induced pluripotent stem cell line from iii), comparing the evaluated VENTX expression in the induced pluripotent stem cell line with VENTX expression in the embryonic stem cell line, and selecting the induced pluripotent stem cell line as a pluripotent stem cell line suitable for clinical use if the VENTX expression in the induced pluripotent stem cell line comprises a level equivalent to that in the embryonic stem cell line.

2. The method of claim 1, wherein said evaluating step of ii) comprises performing one or more of: single telomere vi) selecting the induced pluripotent stem cell line as a pluripotent stem cell line suitable for clinical use based on the genomic integrity result.

6. The method of claim 1, wherein the induced pluripotent stem cell line in iii) is selected if the evaluated telomere length comprises a mean telomere restriction fragment length of about 12 to about 21 kilobases (kb).

7. The method of claim 1, further comprising evaluating telomerase activity in the induced pluripotent stem cell line, comparing the evaluated telomerase activity in the induced pluripotent stem cell line with telomerase activity in an embryonic stem cell line, and selecting the induced pluripotent stem cell line as a pluripotent stem cell line suitable for clinical use if the evaluated telomerase activity in the induced pluripotent stem cell line comprises a level equivalent to that in the embryonic stem cell line.

8. The method of claim 7, further comprising evaluating VENTX expression in the induced pluripotent stem cell line, comparing the evaluated VENTX expression in the induced pluripotent stem cell line with VENTX expression in a differentiated cell line, and selecting the induced pluripotent stem cell line as a pluripotent stem cell line suitable for clinical use if the evaluated VENTX expression in the induced pluripotent stem cell line comprises a level greater than the level of VENTX expression in the differentiated cell line.

9. The method of claim 1, further comprising evaluating VENTX expression in the induced pluripotent stem cell line, comparing the evaluated VENTX expression in the induced pluripotent stem cell line with VENTX expression in a differentiated cell line, and selecting the induced pluripotent stem cell line as a pluripotent stem cell line sutiable for clinical use if the evaluated VENTX expression in the induced pluripotent stem cell line comprises a level greater than the level of VENTX expression in the differentiated cell line.

10. The method of claim 3, wherein the reference gene expression level result is from a differentiated cell, wherein the expresson of the at least one additional gene in the induced pluripotent stem cell line is elevated relative to the reference gene expression result from the differentiated cell.

11. A method of selecting an induced pluripotent stem cell line having a telomere length that comprises a mean telomere restriction fragment length of about 12 kb or more form a plurality of induced pluripotent stem cell lines, the method comprising:
(a) obtaining a plurality of induced pluripotent stem cell lines;
(b) evaluating expression level of VENTX in the induced pluripotent stem cell lines;
(c) comparing the VENTX expression level result from (b) with VENTX expression level from a differentiated cell line or from an embryonic stem cell, and
(d) selecting an induced pluripotent stem cell line as a induced pluripotent stem cell having a telomere length that comprises a mean telomere restriction fragment length of about 12 kb or more if (i) expression of VENTX in the induced pluripotent stem cell line is elevated relative to VENTX expression level in the differentiated cell; or (ii) expression of VENTX, in the induced pluripotent stem cell line is equivalent to expression of VENTX in the embryonic stem cell.

* * * * *

```
SEQUENCE LISTING

<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
gcgcgtacga caccatcccc                                            20

<210> SEQ ID NO 2
<211> LENGTH: 20
<212> TYPE: DNA
<213> ORGANISM: Homo sapiens

<400> SEQUENCE: 2
aaacgcagga gcagcccgtc                                            20

<210> SEQ ID NO 3
<211> LENGTH: 20
<212> TYPE: DNA
<213> ORGANISM: Homo sapiens

<400> SEQUENCE: 3
accttggctg ccgtctctgg                                            20

<210> SEQ ID NO 4
<211> LENGTH: 24
<212> TYPE: DNA
<213> ORGANISM: Homo sapiens

<400> SEQUENCE: 4
agcaaagcct cccaatccca aaca                                       24
```